United States Patent [19]
Beach et al.

[11] Patent Number: 5,409,010
[45] Date of Patent: Apr. 25, 1995

[54] VECTOR DOPPLER MEDICAL DEVICES FOR BLOOD VELOCITY STUDIES
[75] Inventors: Kirk Beach; John Overbeck, both of Seattle, Wash.
[73] Assignee: Board of Regents of the University of Washington, Seattle, Wash.
[21] Appl. No.: 885,803
[22] Filed: May 19, 1992
[51] Int. Cl.[6] .................................................. A61B 8/06
[52] U.S. Cl. ................................................ 128/661.09
[58] Field of Search ......... 128/660.05, 661.08–661.10, 128/662.04; 73/861.25

[56] References Cited

U.S. PATENT DOCUMENTS

| | | | |
|---|---|---|---|
| 3,987,673 | 10/1976 | Hansen | 73/194 A |
| 4,062,237 | 12/1977 | Fox | 128/662.04 X |
| 4,217,909 | 8/1980 | Papadofrangakis et al. | 128/661.09 X |
| 4,265,126 | 5/1981 | Papadofrangakis et al. | 128/661.09 X |
| 4,630,612 | 12/1986 | Uchida et al. | 128/661.09 X |
| 5,014,710 | 5/1991 | Maslak et al. | 128/661.09 X |

OTHER PUBLICATIONS

R. E. Daigle, C. W. Miller, M. B. Histand, F. D. McLeod and D. E. Hokanson; Nontraumatic Aortic Blood Flow Sensing by Use of an Ultrasonic Esophageal Probe, Journal of Applied Physiology 38: 1153–1160; 1975.
M. K. Eyer, M. A. Brandestini, D. J. Phillips, D. W. Baker; Color Digital Echo/Doppler Image Presenatation; Ultrasound in Medicine and Biology, vol. 7, No. 1, pp. 21–31, Jan., 1981.
M. D. Fox; True Volume Flow Measurement with Multiple Beam Ultrasound Doppler, Proceedings of the Thirteenth Annual Northeast Bioengineering Conference, Institute of Electrical and Electronics Engineers Press, 2:357–360; 1987.
D. L. Franklin, D. W. Baker, R. M. Ellis, R. F. Rushmer; A Pulsed Ultrasonic Flowmeter; Institute of Radio Engineers: Transactions on Medical Electronics vol. 6 pp. 204–206, 1959.
P. L. Hansen, G. Cross, and L. H. Light; Beam–angle Independent Doppler Velocity Measurement in Superficial Vessels, Clinical Blood Flow Measurement, J. P. Woodcock, Editor, Sector Publishing, 1974.
D. N. Ku, D. J. Phillips, D. P. Giddens, and D. E. Strandness, Jr., Hemodynamics of the Normal Human Cartoid Bifurcation: in Vitro and in Vivo Studies, Ultrasound in Medicine and Biology, 11:13–26; 1985.
R. C. Nealeigh, C. W. Miller, F. D. McLeod, Jr.; Venous Ultrasound Catheter–tip Technique for Evaluation of Arterial Hemodynamics, Journal of Applied Physiology, 41:6 pp. 946–952, Dec., 1976.
R. S. Reneman, T. VanMerode, P. Hick, A. P. Hoeks; Cardiovascular Applications of Multi–gate Pulsed Doppler Systems; Ultrasound in Medicine and Biology, vol. 12, No. 5, pp. 357–370, May 1986.
R. Satomura; Ultrasonic Doppler Method for the Inspection of Cardiac Functions Journal of the Acoustical Society of America: 29:1181–1185, 1957.
P. A. Stonebridge and C. M. Brophy, Spiral Laminar Flow in Arteries?, The Lancet, vol. 338, Nov. 30, 191, pp. 1360–1361.
D. E. Strandness, Jr., J. W. Kennedy, T. P. Judge, F. D. McLeod: Transcutaneous Direction Flow Detection: A Preliminary Report, American Heart Journal, 78:1, pp. 65–74, Jul. 1969.
S. Uematsu; Determination of Volume of Arterial Blood Flow by an Ultrasonic Device, Journal of Clinical Ultrasound, vol. 9, pp. 209–216, Jun. 1981.
W. Wei14 qi and Y. Lin–xin, A Double Beam Doppler Ultrasound Method for Quantitative Blood Flow Velocity Measurement, Ultrasound in Medicine and Biology, vol. 8, No. 4, pp. 421–425, 1992.
T. L. Yearwood and K. B. Chandran; Physiological Pulsatile Flow Experiments in a Model of the Human Aortic Arch; Journal of Biomechanics, vol. 15, No. 9, pp. 683–704, 1984.

Primary Examiner—Francis Jaworski
Attorney, Agent, or Firm—Robert W. Beach

[57] ABSTRACT

An ultrasonic pulse-echo medical device for determining the angular heading and magnitude of the velocity of blood flowing through a blood vessel by transmitting a pulsed ultrasonic beam from a single transmitting transducer and receiving echoes from sample volumes along such beam by a plurality of ultrasound receiving transducers. Independent motions in the same sample volume, such as those of a moving vessel wall and the motion of blood flowing through the blood vessel, can be separately analyzed and displayed.

3 Claims, 17 Drawing Sheets

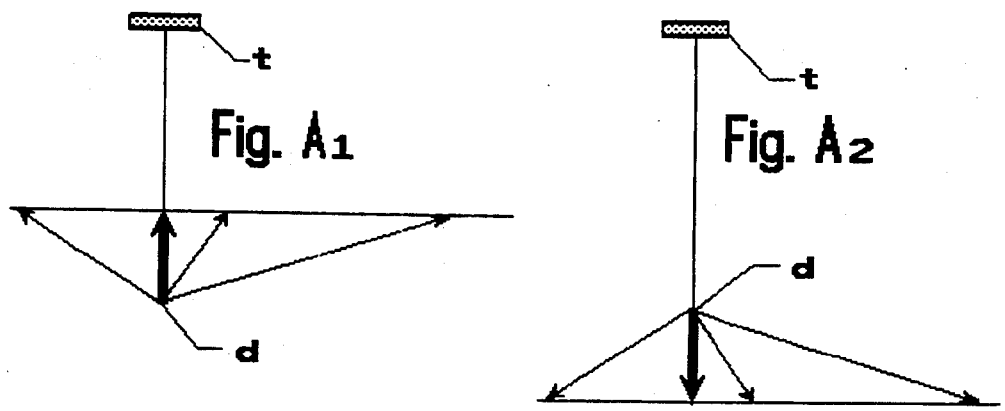
Fig. A1   Fig. A2
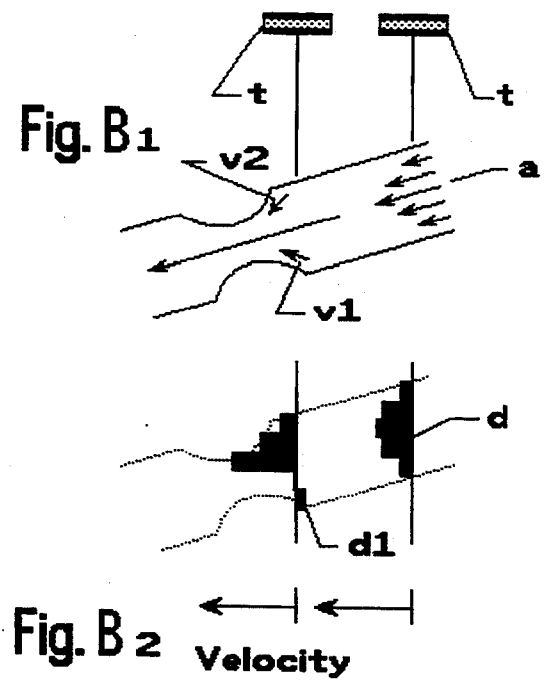
Fig. B1
Fig. B2  Velocity

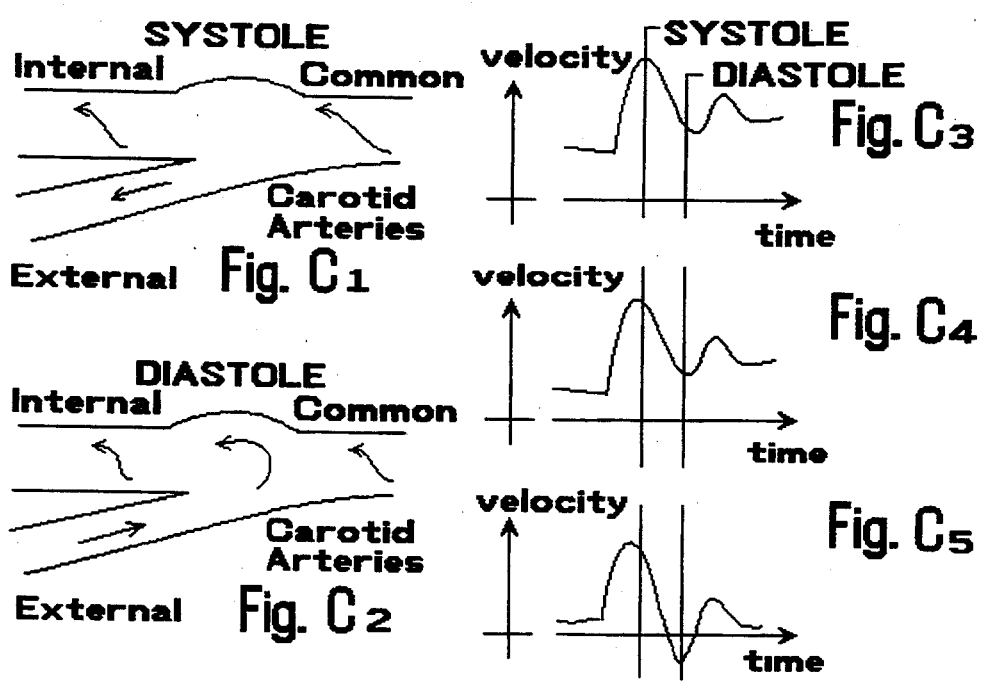
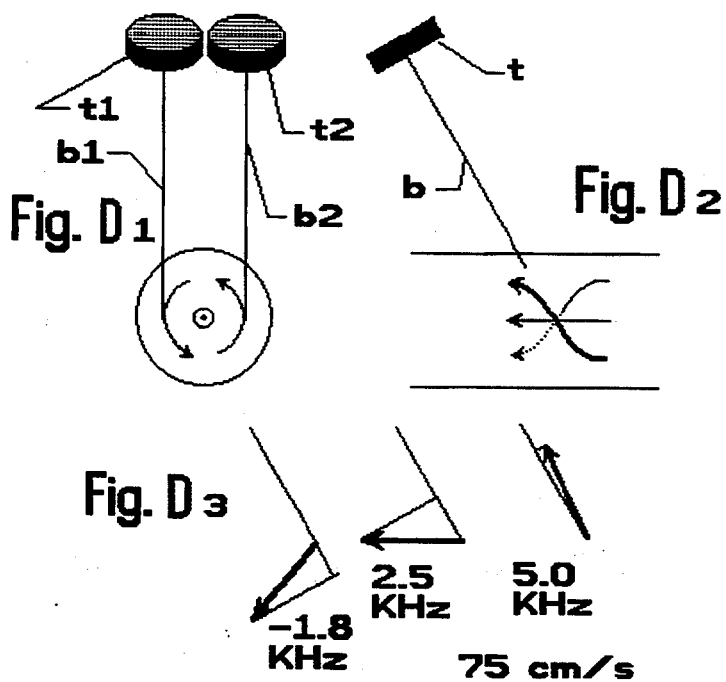

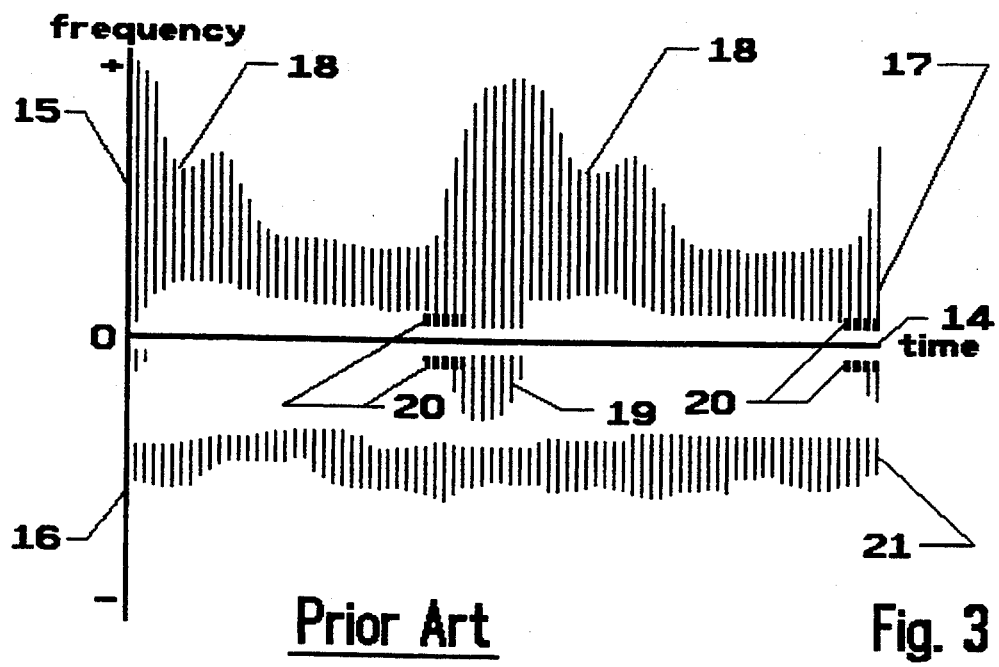
Prior Art   Fig. 3
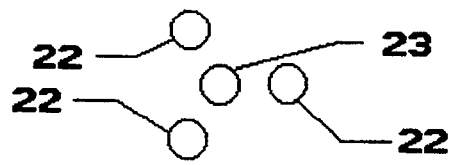
Fig. 4A
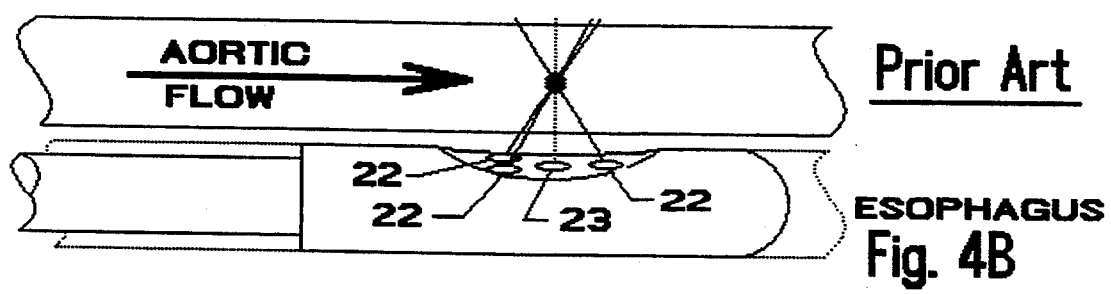
Prior Art
Fig. 4B

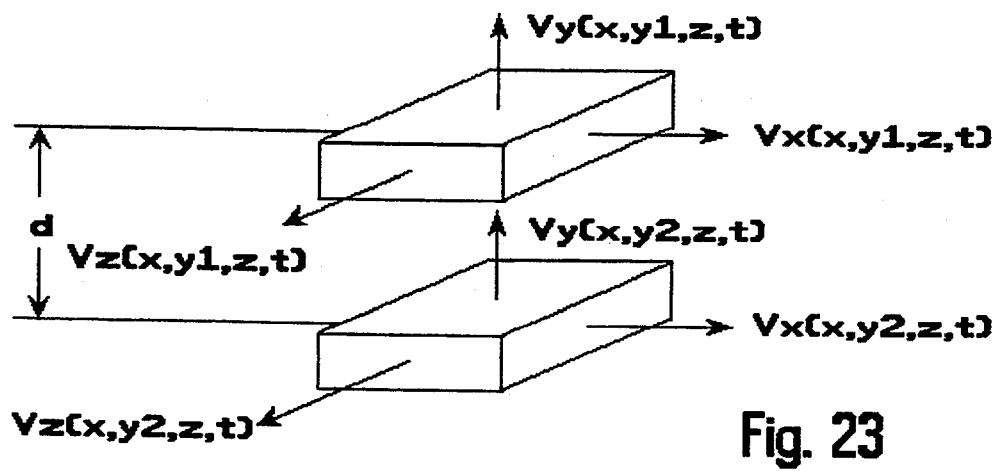
Fig. 23
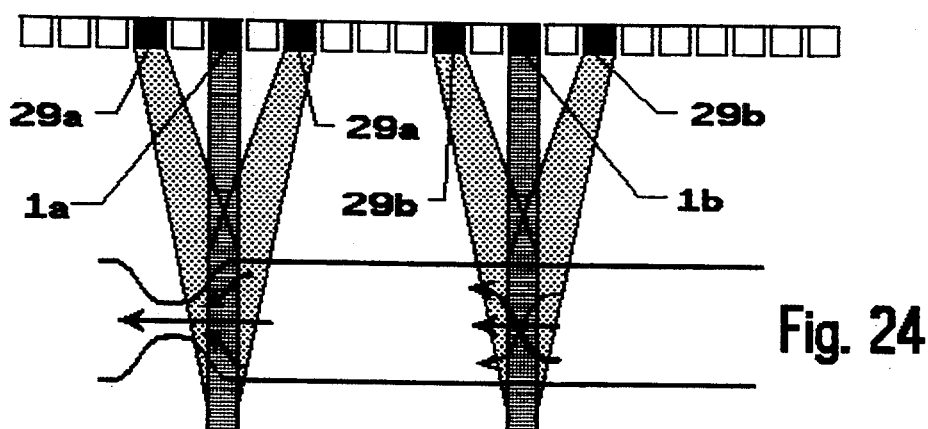
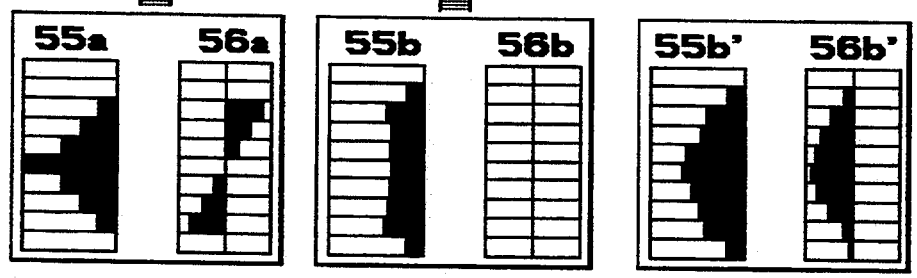
Fig. 24

VECTOR DOPPLER MEDICAL DEVICES FOR BLOOD VELOCITY STUDIES

This invention was made with government support under grant numbers 5 RO1 HL 20898, 1 P50 HL 42270 awarded by the National Institutes of Health. The government has certain rights in the invention.

FOREWORD

Definitions of Terms used in the specification follow the Detailed Description.

A Bibliography of References follows the Definitions of Terms.

BACKGROUND OF THE INVENTION

1. Field of the Invention

The present invention relates to noninvasive diagnostic medical devices which utilize ultrasound to determine the heading and the speed of blood flowing in a blood vessel or in the heart.

2. Prior Art

The measurement of blood velocity using Doppler shifted ultrasonic echoes has proven clinically useful for the diagnosis of arterial and venous disorders since it's discovery by Koneko and Satamura in Osaka in 1957 (S. Satamura) and by Franklin and Baker in Seattle in 1959 (D. L. Franklin). Blood velocities in depressed, normal and elevated ranges (2 cm/s to 400 cm/s) interact with the wave speed of ultrasound in blood (157,000 cm/s) to create a Doppler frequency shift (0.0025% to 0.5%) in the ultrasound frequency. If the ultrasound frequency is selected for the strongest echoes from blood through the skin (1.5 MHz to 10 MHz), the Doppler frequency is within the normal hearing range of humans (20 Hz to 15,000 Hz) permitting the resultant Doppler signals to be heard.

$$\frac{2 * (\text{Closing Speed})}{\text{Ultrasound Speed in Blood}} = \frac{\text{Audible Doppler Shift Frequency}}{\text{Ultrasound Frequency}}$$

2 accounts for the round trip of the ultrasound
* is the symbol for multiplication The application of ultrasound to blood flowing in arteries is discussed below in connection with diagrams in the drawings illustrating blood flow phenomena in arteries.

BRIEF DESCRIPTION OF DIAGRAMS PERTAINING TO BLOOD FLOW IN ARTERIES

FIG. $A_1$ and FIG. $A_2$ are diagrams indicating the direction of flow of blood through an artery with reference to ultrasound projected into such blood flow.

FIG. $B_1$ and FIG. $B_2$ are diagrams relating to projection of ultrasound into the flow of blood through an artery at the entry to a smooth arterial stenosis.

FIG. $C_1$ and FIG. $C_2$ are diagrams illustrating the flow of blood through a normal carotid artery bifurcation.

FIG. $C_3$, FIG. $C_4$ and FIG. $C_5$ are diagrammatic illustrations of curves representing blood flow velocity in the internal carotid artery, the common carotid artery and the external carotid artery, respectively.

FIG. $D_1$ and FIG. $D_2$ are diagrams illustrating the projection of ultrasound into blood flowing through a straight artery, which blood flow is not straight.

FIG. $D_3$ is a diagram representing different ultrasound doppler frequencies.

Underlined values are outside the human hearing range.

Commercial ultrasonic Doppler and time domain velocimeters measure only the component of velocity aligned with the ultrasound beam. Thus, any one of a number of divergent blood velocity vectors, all generally approaching the ultrasound transducer t (FIG. $A_1$), can result in identical Doppler frequencies d. Similarly any of the divergent blood velocity vectors traveling generally away from the transducer t (FIG. $A_2$) will give identical results d if they have identical projections on the ultrasound beam. Therefore, much of the information about blood flow is absent in conventional Doppler signals. The absent information, if accessed, can be used to eliminate critical diagnostic errors and allows diagnostic parameters to be obtained that are not now available.

DIAGNOSTIC APPLICATION OF BLOOD VELOCITY STUDIES

Ultrasonic medical Doppler devices have been used for the identification and classification of arterial stenoses. Diagnostic errors often result from failure to correctly identify the true direction of blood flow from its effect on Doppler frequencies, One common error occurs at the entry to a smooth arterial stenosis (FIG. $B_1$). In laminar flow through an artery a angled away from the ultrasound transducer t, the Doppler frequencies d (FIG. $B_2$) at shallower and deeper depths can be displayed versus depth (R. S. Reneman). Such different Doppler frequencies are often displayed as different

|  | Depth of Artery | AUDIBLE DOPPLER FREQUENCIES FOR MUSCLE OVERLYING ARTERY | | |
|---|---|---|---|---|
| Blood Velocity | Ultrasound Frequency | 10 cm | 4 cm | 2 cm |
|  | Doppler Shift | 1.5 MHz | 5 MHz | 10 MHz |
| 2 cm/s | Depressed | 0.0025% | 38 Hz | 127 Hz | 255 Hz |
| 100 cm/s | Normal | 0.125% | 1910 Hz | 6370 Hz | 12,738 Hz |
| 400 cm/s | Elevated | 0.5% | 7643 Hz | 25,477 Hz | 50,955 Hz | colors (red and blue) rather than as bars to the right or left representing direction. As the velocity vectors at the entrance to the stenosis tilt toward the orifice, the velocities v1 near the deep wall of the artery tilt upward causing the blood to approach the transducer, and the velocities v2 near the superficial wall of the artery tilt downward. This reversal of the directional Doppler frequency d1 near the deep wall is often misdiagnosed as a reversal in the direction of blood flow and has resulted in cases of misdiagnosis and patient mismanagement.

The most often requested medical ultrasound Doppler examination of the arteries is the examination in the neck of the bifurcation of the carotid arteries which supply blood to the brain. Proper diagnosis of stenoses here is of central importance in the prevention of stroke. Patients with a Doppler frequency shift at the end of diastole indicating blood velocity greater than 140 cm/s have a 50% chance of stroke in two years; if such patients undergo a carotid endarterectomy operation, the chance of stroke in 2 years is reduced to 2%.

In the normal carotid artery bifurcation during the systolic period of the cardiac cycle (FIG. $C_1$) and during the diastolic period of the cardiac cycle (FIG. $C_2$), the common carotid artery C brings blood from the heart (from the right) in systole Cs and diastole Cd; the internal carotid artery I carries the blood on toward the brain in systole Is and diastole Id, the external carotid artery E carries blood on toward the face in systole Es but in the early period of diastole, flow in the external carotid is reversed Ed. These velocity characteristics are usually seen on velocity waveforms from the internal carotid artery I (FIG. $C_3$), the common carotid artery C (FIG. $C_4$) and the external carotid artery E (FIG. $C_5$). Elevation of the waveform tracing above the abscissa represents forward flow; reverse flow in the external carotid Ed (FIG. $C_5$) is indicated by depression of the tracing at that time point.

The presence of a dilatation at the bifurcation, called the carotid bulb, and the period of flow reversal isolated to the external carotid artery Ed are associated with extremely complex flow patterns in the bifurcation region. One purpose of the Vector Doppler of the present invention, is to explore the details of the complex hemodynamics of this bifurcation, and use that information for diagnosing early atherosclerotic obstructive disease that may lead to stroke and for exploring the relationship between hemodynamics and formation of atherosclerosis.

Using ultrasonic Doppler devices, a number of diseases of arteries, veins and the heart can be diagnosed:

Deep Venous Thrombosis of the Leg (thrombophlebitis): Abnormal proximal venous obstruction is detected by observing that the venous flow velocity does not vary with respiration, implying high distal venous pressure;

Venous Valvular Incompetance of the Leg: Abnormal venous reflux is detected by observing that compression of the leg proximal to the measurement site results in blood flow backwards through the valves. This blood flow can be detected with a Doppler device. Release of distal compression also results in reflux detectable by a Doppler device;

Atherosclerosis: Abnormal arterial obstruction is detected by the loss of the normal biphasic pulsatile arterial Doppler signal distal to the obstruction, elevated local Doppler frequencies implying high blood velocities through a stenosis, and depressed distal systolic blood pressure detected using a blood pressure cuff/sphygmomanometer and Doppler device for endpoint detection;

Aortic Valve Stenosis: Abnormally high systolic blood velocities through the aortic valve indicate stenosis. The pressure drop across the stenotic valve can be computed from the Doppler velocity, $p=4 (mmHg/(M^2/s^2)*V$; and Cardiac Valve Regurgitation: Detection of blood velocities through the aortic or pulmonic valves during diastole or detection of blood velocities through the mitral or tricuspid valves during systole; flow is in the wrong direction.

Complexity of Blood Normal Flow

Even straight arteries have complex helical flow (P. A. Stonebridge). When conventional Doppler instruments are applied to this helical flow (FIGS. $D_1$ and $D_2$), widely different velocity measurements result from slight angularion of the Doppler transducer t (FIG. $D_2$). If the transducer t1 is positioned and angled so that the ultrasound beam b1 intersects the descending portion of the helix, the directional Doppler frequency may be negative (FIG. $D_3$). If the transducer t2 is positioned and angled so that the ultrasound beam b2 intersects the ascending portion of the helix, the directional Doppler frequency will be positive and greater than expected from an independent knowledge of the midstream velocity (FIG. $D_3$). The pitch angle of normal helical blood flow varies during the cardiac cycle, sometimes reaching angles of 80 degrees with the vessel axis. In order to minimize variability in Doppler measurements, the examiner adjusts the angle of the scan plane to obtain the greatest possible Doppler frequency, which results in acquiring the Doppler data from the portion of the helix which is most closely aligned with the ultrasound beam b2.

Doppler signals always contain a range of frequencies. Rather than the average value; the highest value is used to determine a diagnosis, because it is the most consistent. For diagnostic purposes, this numeric value is compared to empirically derived criteria. This numeric value, adjusted for examination angle, has never been successfully used in computations such as determining the correct volumetric blood flow rate, so volumetric blood flow rate has not been useful in reaching a diagnosis.

Recognizing this limitation, a series of devices have been developed to measure a selected component of blood velocity parallel to the artery axis including devices by Hansen, Uematsu, Wei-qi, and Fox. All of these devices ignore the problem of helical blood flow and other complex blood flow patterns. Nealeigh, and Daigle have both constructed Doppler devices designed to explore the 3 dimensional vector nature of blood flow. Their devices were cumbersome, limited to unacceptably low data acquisition rates, limited to use for a single sample volume, and subject to refractive errors in use. None of the devices developed previously can be modified for implementation in modern ultrasound instruments.

Prior Use of Ultrasonic Doppler Diagnostic Devices

Since the introduction of Doppler blood velocimeters for cardiac and vascular applications, various improvements have been developed. The original systems used continuous wave ultrasound transmitters and received continuous echoes from the tissues combining signals from all depths (CW Doppler). The introduction of quadrature demodulation by McLeod permitted the separation of Doppler echoes shifted toward higher frequencies, representing blood flow toward the ultrasound transducers, from Doppler echoes shifted toward lower frequencies, representing blood flow away from the transducers. This is called directional or bidirectional Doppler (D. E. Strandness).

When pulsed Doppler was introduced, the examiner was able to select the depth in tissue from which the Doppler shifted echo signal was reflected. The device which selected the depth is called the sample gate. The earliest pulsed Doppler systems had only a single gate;

later, multigate pulsed Dopplers were constructed which permitted the simultaneous acquisition of Doppler frequencies from several different depths which displayed the velocities at different depths as tracings (R. S. Reneman) or colors (M. K. Eyer).

The introduction of the electronic Doppler frequency measurement systems permitted the creation of displays of Doppler frequencies from a single gate Doppler instrument. The first frequency measurement systems determined a single Doppler frequency in the signal for each moment (0.01 seconds) in time. Such systems were used to create Doppler waveforms, Doppler frequency on the ordinate versus time in the cardiac cycle on the abscissa. Later, Doppler spectrum analyzers were used with single gate Doppler instruments to measure the power of each Doppler frequency present for each moment in time. Such systems were used to create spectral waveforms, permitting the identification of more complex flow conditions in which multiple velocities are present in the sample volume in one moment in time.

Multigate Doppler systems were used to create two styles of two dimensional displays using electronic Doppler frequency analyzers. None of the instruments used a Doppler spectrum analyzer; all operate as if only one Doppler frequency, and therefore one blood velocity, is present in each Doppler sample volume at a time. In one type of display, data is shown from a single ultrasound beam penetrating tissue. The vertical dimension on the Doppler M-mode video display represents depth in the tissue; the horizontal dimension on the Doppler M-mode video display represents time in the cardiac cycle. Doppler frequency, representing velocity, is shown at each depth and each time on the video display either as the displacement of a line (R. S. Reneman) or as one of a series of color (M. K. Eyer). Another type of display is the two dimensional display in which the data from a plane transecting tissue at a single time is shown. The vertical dimension on the two-dimensional flow video image represents depth in the tissue; the horizontal dimension on the two-dimensional flow video image represents lateral location in tissue. Doppler frequency, representing velocity, is shown at each depth and each lateral location time on the video display as one of a series of color (M. K. Eyer).

The single directional Doppler frequency corresponding to each location in the image may be shown as a lateral displacement of a portion of a vertical grid line on the image (R. S. Reneman) or as a color of a portion of a vertical line on the image (red for flow in one direction, blue for flow in the other direction)(M. K. Eyer).

BRIEF DESCRIPTION OF DRAWINGS OF THE PRIOR ART

FIG. 3 is a diagram representing the spectral waveform display generated by a conventional single sample gate bidirectional pulsed Doppler device.

FIG. 4A is a diagrammatic plan of a scanhead for a 3-dimensional Doppler device with one imaging transceiver and three pulsed Doppler transceivers which operate independently; and FIG. 4B is a diagrammatic elevation of such device showing intersecting beam patterns.

SPECIFIC PRIOR ART DOPPLER DEVICES

Figure 1:
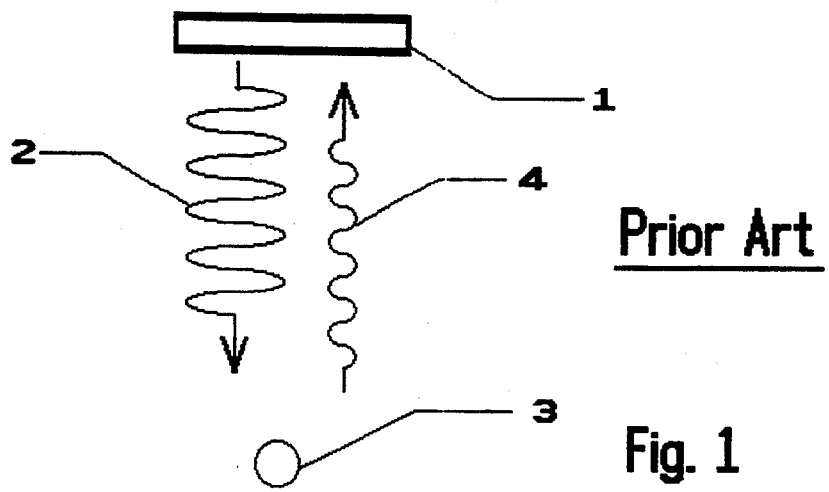
FIG. 1 is a diagrammatic representation of a pulse of ultrasound transmitted into a patient's body by an ultrasonic Doppler medical device and the resulting echo.

When an ultrasound transmitting transducer 1 (FIG. 1) transmits a pulse of ultrasound 2 into tissue, echogenic targets 3 return echoes 4 to a receiving transducer which may be the transmitting transducer or may be a separate transducer adjacent to the transmitting transducer. The time of arrival of an echo from a target at a particular depth can be computed using the speed of ultrasound in tissue and the depth of the target. The echo contains information about the echogenicity of the target (echo amplitude) and the relative position of the target (echo phase). An ultrasonic pulsed Doppler compares the phase of each of the echoes from a series of pulse-echo cycles; a progressive phase shift indicates travel with respect to the ultrasound transducers; the distance of travel between pulse-echo cycles divided by the time between pulse-echo cycles gives the speed of the target toward or away from the transducers.

Figure 2:
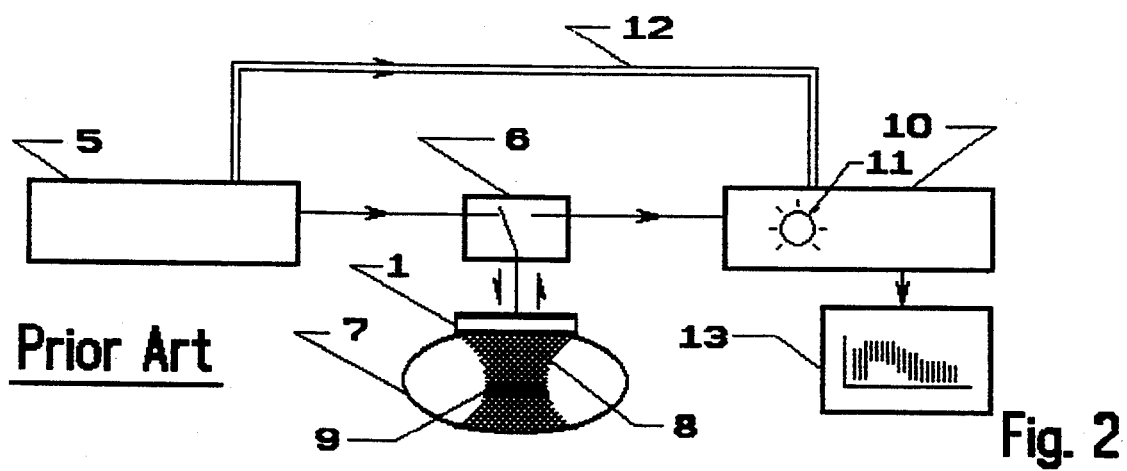
FIG. 2 is a schematic block circuit diagram of the components of a conventional single sample gate bidirectional pulsed Doppler device generating the pulse and receiving the echo represented by the diagram of FIG. 1.

In the Doppler instrument (FIG. 2), an ultrasonic frequency pulse generator 5 operating in the radio frequency range (2 MHz to 20 MHz) sends each pulse to the ultrasound transducer 1 via the transmit-receive switch 6. The transducer, which is in contact with the skin of the patient's body 7, forms an ultrasound beam 8 which penetrates into the patient's body. An echo from the sample volume 9, which contains information from the targets of interest in the sample volume, is received by the transducer 1, and the portion of the echo with sample volume data is selected by the ultrasound Doppler receiver 10 by adjusting the delay between the time of pulse transmission and the time of receiving the selected echo portion 11. A reference quadrature radio frequency signal 12 from the pulse generator 5 is sent to the receiver to permit quadrature phase demodulation of each selected echo portion 11. A typical pulse Doppler instrument will process 12,800 pulse-echo cycles per second (PRF=12.8 KHz). Echoes from 128 pulse-echo cycles received over a period of 0.01 seconds are combined to make a single line spectrum in the spectral waveform display shown in FIG. 3.

Color Doppler and time domain color flow instruments use similar pulse repetition frequencies (PRF=12.8 KHz for a 5 cm depth), but the number of pulse-echo cycles used for determination of the blood velocity component may be as few as four, received over a period of 0.3 ms in time or as many as thirty-two, received over a period of 2.4 ms.

A typical graphical presentation of Doppler signals is shown in FIG. 3 as a spectral waveform developed from left to right along the abscissa 14 which represents time in the cardiac cycle, the ordinate 15 above the abscissa 14 represents the velocity components toward the transducer and the ordinate 16 below the abscissa 14 represents the velocity components away from the transducer. The waveform is created by displaying a group of individual spectra 17, each parallel to the ordinate. If the sample volume spans the wall separating an adjacent artery and vein so that flows in both the artery and vein are included, the spectral waveform will resolve signals from the artery, from the vein, and from the artery and vein walls. By recognizing the characteristic shape of the waveform, the arterial, venous and wall signals can be differentiated.

The arterial signals 17, 18, 19 are identified on the basis that the major velocity component of blood velocity in the artery is directed toward the ultrasound transducer which is held by the examiner so that the ultrasound beam is tilted toward the heart and that it has high velocity periods representing systole with intervening low velocity periods representing diastole. These periods are synchronized with the cardiac cycle; the waveform depicted represents two cardiac cycles. A dicrotic wave 18 in the forward flow direction at the end of the systolic period indicates a normal signal for an, artery supplying the brain or kidney. Flow reversal may be present in any arterial signal during the early portion of the systolic period 19 representing complex flow. Reverse flow is usually present in peripheral arteries supplying resting tissues during the transition from systole to diastole due to normal wave reflection from the constricted precapillary sphincters which restrict blood flow to those tissues that are not in need of it.

At the onset of systole, the arterial wall motion due to the rapid expansion of the arterial diameter creates low frequency nondirectional Doppler signals. These can be identified on the spectral waveform display as low frequency, high strength signals 20 which are symmetrical above and below the abscissa.

The venous flow spectral waveform 21 can be differentiated from arterial flow spectral waveform on the display because of the direction of velocity components away from the transducer indicating flow toward the heart portrayed below the abscissa 14, the lack of pulsations synchronized with the cardiac cycle, and the phasic changes in velocity synchronized with respiration, indicating a low pressure blood vessel.

The Problem of Measuring Arterial Flow Velocities

Although conventional Doppler analysis has great clinical utility, logical applications for Doppler velocity measurements have proven unreliable when existing instruments are used in an attempt to determine the velocity of blood flow through an artery or vein. Theory suggests that arterial and venous volumetric flowrates can be computed from the measured Doppler velocity multiplied by the measured vessel cross sectional area. This measurement has worked well when applied to the volumetric flow rate through the aortic valve of the heart (cardiac output), but has failed when applied to the measurement of localized flowrate along a specific section of an artery at a distance from the heart. This failure can be traced to the erroneous assumption that the flow of blood in an artery is always parallel to the axis of the vessel.

Yearwood (T. L. Yearwood) and Ku (D. N. Ku), as well as more recent authors (P. A. Stonebridge), have shown that the normal flow in most arteries is helical, not parallel to the vessel axis, due to the effect of bends and bifurcations in the artery. The normal arterial flow is much like the whirlpool which is formed by water as it drains from a kitchen sink.

Although blood does flow parallel to the walls of an artery in the regions near its walls, this does not mean that even these velocities are parallel to the axis of the artery as shown in FIG $D_1$. Thus, it is not possible, using the definition of the cosine of an angle, to determine correctly the magnitude of the velocity from a measurement of the vector component of the velocity projected onto the ultrasound pulse-echo beam path, because the angle between the velocity vector and the ultrasound beam along which a component of the velocity is measured is not known.

Prior Art Attempts at Solutions to the Problem

Previous investigators, recognizing that some problem existed in determining the true course of blood flowing through an artery, have made attempts to adjust for the angle between the local direction of blood flow and the path of the ultrasonic beam, or to measure the velocity of blood flow through arteries in three dimensions.

Figure 5:
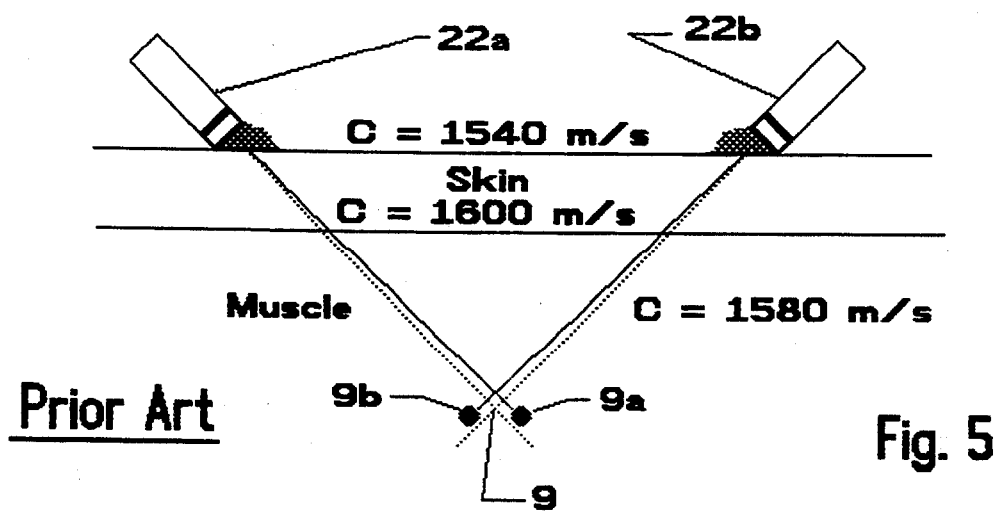
FIG. 5 is a diagram representing the error in sample volume registration which results from using independent pulsed Doppler transducers through skin and muscle.

A two dimensional device was developed by Nealeigh (R. C. Nealeigh) and extended to three dimensions by Daigle. The Daigle device (R. E. Daigle) shown in FIG. 4A and FIG. 4B used three independent Doppler transceivers 22 and one imaging transceiver 23 intersecting at a common point to determine three components of the velocity vector at a single point in the sample volume. This method is limited because:

1) each of the three Dopplers must operate independently interleaving transmit pulses, thus reducing the PRF from each by a factor of three;
2) the required assumption that a single velocity vector is present in the sample volume during the period of measurement is not valid on either temporal or spatial grounds. Blood velocity vectors can change rapidly: at the onset of systole when high accelerations are present and at the end of systole when decelerations result in unstable flows. Doppler sample volumes are often much larger than expected, with current linear array electronic scanheads each Doppler sample volume may be 1 cm thick and span several flow regions; and
3) refractive and range errors will prevent the ultrasound beam patterns of the three Doppler transducers from intersecting at a common sample volume 9 in most applications as illustrated in FIG. 5. The beam patterns from the Doppler ultrasound transducers 22a and 22b are adjusted for angle and range to intersect at a common sample volume 9 for a speed of ultrasound of 154,000 cm/sec in tissue. Ultrasound often traverses tissues with other ultrasound speeds including fat (145,000 cm/sec) and Muscle (158,000 cm/sec).

According to Snell's Law, as the ultrasound passes at an acute angle through an interface between one tissues and another in which the speed of ultrasound differs, refractive bending occurs. If the speed in the second tissue is higher than the first, the ultrasound beam will be bent to travel more parallel to the interface. In addition, the depth of the sample volume will be greater when the ultrasound speed is greater. The two effects will combine to cause the sample volume 9a from the left transducer 22a to be displaced to the right and the sample volume 9b from the right transducer 22b to be displaced to the left, resulting in a failure of the sample volumes to coincide.

Another version of the independent multibeam system was reported by Wei-qi (W. Wei-qi). In this device, dual continuous wave Doppler beams are angled to intersect at a common point. After Doppler demodulation to determine the velocity component viewed by each beam, the nondirectional values are subtracted; a zero result indicates that the two Doppler beams are at equal opposing angles to the blood flow and therefore the bisector of the angle between the beams is perpendicular to the blood velocity vector. From this orientation, the magnitude of the vector can be determined from the Doppler frequency extracted from either Doppler beam since the angle between the beams is known. This works well if the heading of the blood velocity vector is constant, however, it is changing constantly with time in the cardiac cycle.

Figure 6:
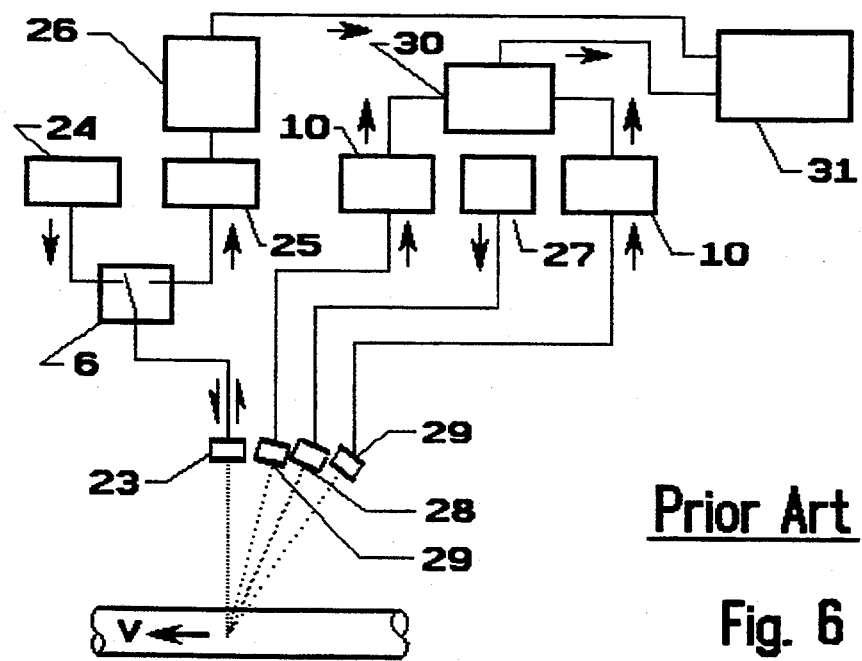
FIG. 6 is a schematic block diagram of an ultrasonic Doppler blood flowmeter with an imaging transceiver, a Doppler transmitting transducer and two Doppler receiving transducers.

The Uematsu device (S. Uematsu) shown in FIG. 6 used a fixed angle ultrasound system to measure arterial volumetric flowrate. One portion of the system for measuring the arterial diameter included an imaging transmitter 24 with an imaging transducer 23 for projecting an ultrasound beam into an artery and receiving echoes from that artery, a receiver 25 and a processor 26 to determine arterial diameter. A continuous wave ultrasonic generator 27 was connected to a transmitting transducer 28 located between a pair of adjacent receiving transducers 29 connected to Doppler receivers 10 to determine an "average" velocity computed by a processor 30. The volumetric flow rate in the artery was computed in a processor 31 which combined the information from the arterial diameter processor 26 and the Doppler velocimeter processor 30. This method resulted in inaccurate or unusable results because:

1) the spatial distribution of the velocities within the sample volume were not known; and
2) the algorithm for computing velocity included an implicit assumption that the angle with the blood flow vector was known and constant, an assumption that is not true in normal helical flow.

Figure 7:
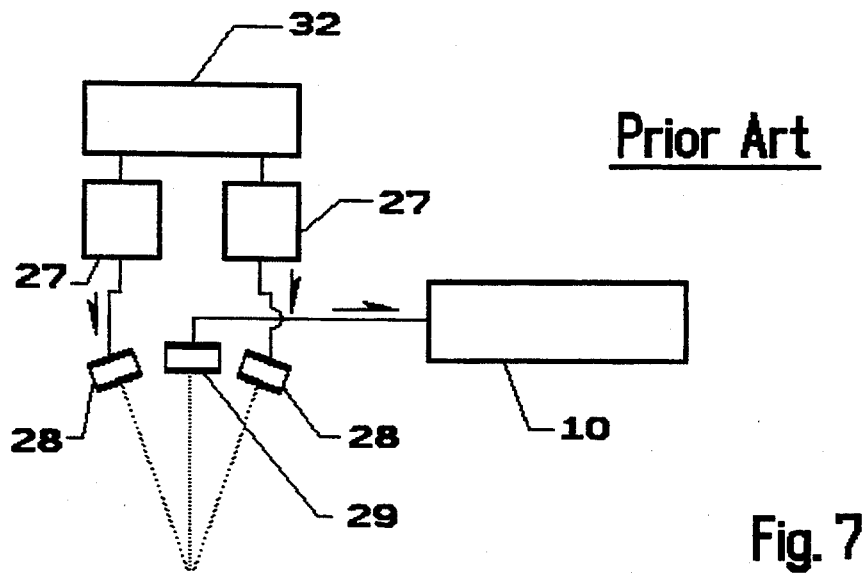
FIG. 7 is a schematic block diagram of a dual transmitter ultrasonic Doppler device for determining blood velocity components perpendicular to the receiving transducer beam pattern.
Figure 8:
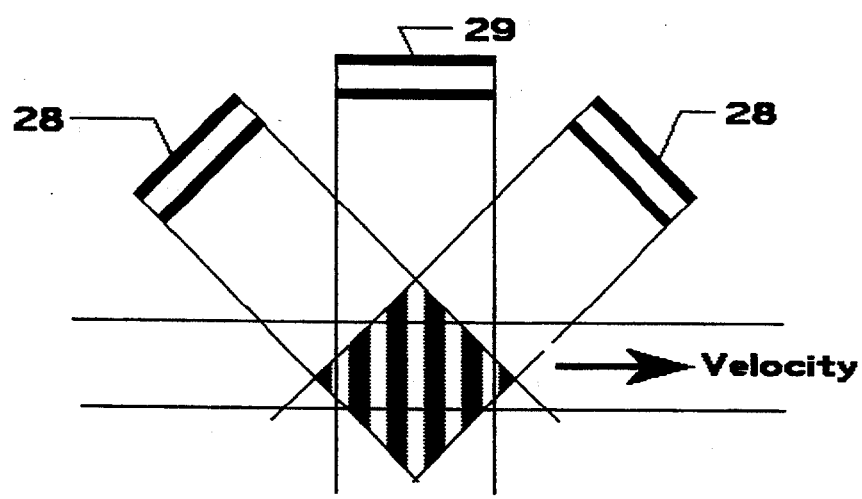
FIG. 8 is a diagram representing the ultrasound field pattern generated by the dual transmitter ultrasonic Doppler device shown in FIG. 7.

The Hansen device (P. L. Hansen) (Per Loubaerg Hansen, Ultrasonic Transducer Devices, U.S. Pat. No. 3,987,673, issued Oct. 26, 1976) shown in FIG. 7 attempted to measure the component of the velocity along the axis of the artery by using a pair of continuous wave ultrasonic generators 27 driving ultrasound transmitting transducers 28 to produce intersecting beam patterns. The two beams established an interference pattern shown in FIG. 8 with planes of interference perpendicular to the artery axis. Erythrocytes traversing the interference pattern scatter an amplitude modulated ultrasound echo signal to the receiving transducer 29 and receiver 10. The frequency of amplitude modulation was proportional to the velocity of the erythrocytes perpendicular to the planes of the interference pattern.

When the transducer array was placed with a blood vessel passing through the sample volume where the interference pattern was present, and oriented so that the vessel axis was perpendicular to the planes of the interference pattern, the component of the blood velocity along the vessel axis was obtained. The Doppler signal was nondirectional. Although Hansen suggested that the roles of the transmitting transducers and the receiving transducer could be exchanged, he did not suggest that such an exchange, with proper directional demodulation, would permit the direction of the velocity vector to be obtained. Hansen did not suggest the greatest advantage of using a single transmitting transducer, that then any number of receivers could be used simultaneously at any locations, each obtaining a different component of velocity.

This CW Doppler system was improved by Fox (M. D. Fox) (Martin D. Fox, Crossed Beam Ultrasonic Flowmeter, U.S. Pat. No. 4,062,237, issued Dec. 13, 1977) to provide a directional signal by controlling the two ultrasound frequency generators 27 with a master control 32 shown in FIG. 7 which made the frequency of one transmitter lower than the other. The interference pattern moved toward the side of the lower frequency transmitting transducer to produce an amplitude modulated audio oscillation in the ultrasound echoes from stationary erythrocytes. Erythrocytes traveling toward the side of the higher frequency transmitter generated echoes with an amplitude modulated audio oscillation of increased frequency; erythrocytes traveling toward the side of the lower frequency transmitter generated echoes with an amplitude modulated audio oscillation of decreased frequency. Implementation of the system was impractical on modern multipurpose linear array and phased array scanheads. In addition, obtaining the optimal orientation for the vector component required proper alignment of the ultrasound transducers with the blood vessel, a process that is difficult if the vessel is not parallel to the skin of the patient.

Neither Hansen nor Fox suggest that pulsed Doppler methods could be used.

Despite all of the improvements in Doppler instruments, all known prior art devices except the device by Daigle (FIGS. 4A and 4B) are limited to the measurement of one component of the blood velocity which is determined by the placement of the transducers. Conventional ultrasound velocity systems provide useful quantitative data only when the blood velocity axis is known to be parallel to the ultrasound beam, such as during the examination of the origin of the aorta viewed from the suprasternal notch, and the examination of the mitral valve when viewed from the esophagus. The systems by Uematsu, Wei-Qi, Hansen and Fox provide useful quantitative data only when the blood velocity axis is known to be parallel to the skin, and in addition when the examination plane is known to be parallel to the velocity. Actually, arteries and veins have complex courses, and in the arteries helical flow is universally present.

Current commercial Doppler instruments contain computer programs to assist the examiner when computing the "magnitude" of the blood velocity by dividing the measured component of the velocity by the cosine of the examination angle between the supposed true vector heading and heading of the measured component of the velocity along the heading of the ultrasound beam. In most cases, repeating the measurement at the same arterial location using a different examination angle results in a different answer. A decade of evidence has accumulated which proves that the true heading of the velocity vector cannot be assumed, even when the orientation of the vessel walls is known, and the velocity heading changes during a single cardiac cycle.

Although the Daigle device is designed to obtain the heading and magnitude of the velocity vector, it is limited to acquiring a single vector at a time, it is limited to a single sample volume, because of the need to transmit separately from each transducer, it has inadequate data acquisition rates and inadequate correlation between the data gathered from each view, and finally, the design cannot be implemented easily on current commercial scanheads.

Problem Solved by the Present Invention

1) The problem is to determine the headings and magnitudes of multiple blood velocity vectors within each selected sample volume with a pulsed Doppler system.
2) A further problem is to measure simultaneously the velocity vectors in multiple sample volumes along the beam pattern of a single ultrasound transmitting transducer and display the velocities as a function of depth and time in a manner similar to the display methods used for single component multigate Doppler M-mode or color velocity M-mode.
3) A further feature of the problem is to be able to determine the blood flow heading and to measure the magnitude of the blood velocity in a sample volume near the vessel wall where low velocity blood in the boundary layer is often rejected by a high pass filter circuit intended to reject motions of the artery wall.
4) A further feature of the problem is to determine the components of the velocities that are perpendicular to a cross section of the artery for computing the volumetric flow rate in the artery.
5) A further feature of the problem is to determine the magnitude of the velocity of the Bernoulli pressure depression that is the driving force for the closure of venous valves and the driving force for effecting catastrophic hemorrhage within atherosclerotic plaques.

SUMMARY OF THE INVENTION

Objects of the present invention are:
1) to be able to determine the depth location of regions where blood flow is present;
2) to be able to determine the heading of a blood velocity vector in localized blood flow and its magnitude in two dimensions or in three dimensions;
3) to be able to detect the presence of multiple blood velocity vectors in a single sample volume simultaneously and to resolve independently the magnitudes and headings of each velocity vector using backprojection algorithms;
4) to be able to determine the headings and magnitudes of velocity vectors simultaneously in multiple sample volumes along the line of the ultrasound transmit beam;
5) to use the capability of identifying multiple velocity vectors for sample volumes near an artery wall to detect the independent vectors representing blood velocity and wall motion, permitting the separation of those signals on the basis of heading of motion as well as on the basis of speed;
6) to accomplish all of the foregoing objects without a reduction in PRF and therefore without an increased chance of aliasing;
7) to use the appropriate projections of the velocity vector magnitude and angle and changes in the magnitude and angle to automatically compute volumetric flow rate, Bernoulli pressure depression and rate of energy loss in blood vessels;
8) to minimize refractive errors in position and alignment of the effective sample volumes; and
9) to perform the measurements by observing a sample volume through a single viewing window of minimum size.

The foregoing objects can be accomplished by the use of a pulsed Doppler with a single transmitter, multiple receivers and backprojection of the resultant Doppler shifts from one sample volume detected by the multiple receivers. Although developed using Doppler demodulation, the method is equally applicable to time domain blood velocity measurements. If the velocity angle and magnitude are required in only two dimensions, the method can be implemented using a conventional high density linear array ultrasound scanhead configuration.

BRIEF DESCRIPTION OF THE DRAWINGS OF THE INVENTION

Figure 9:
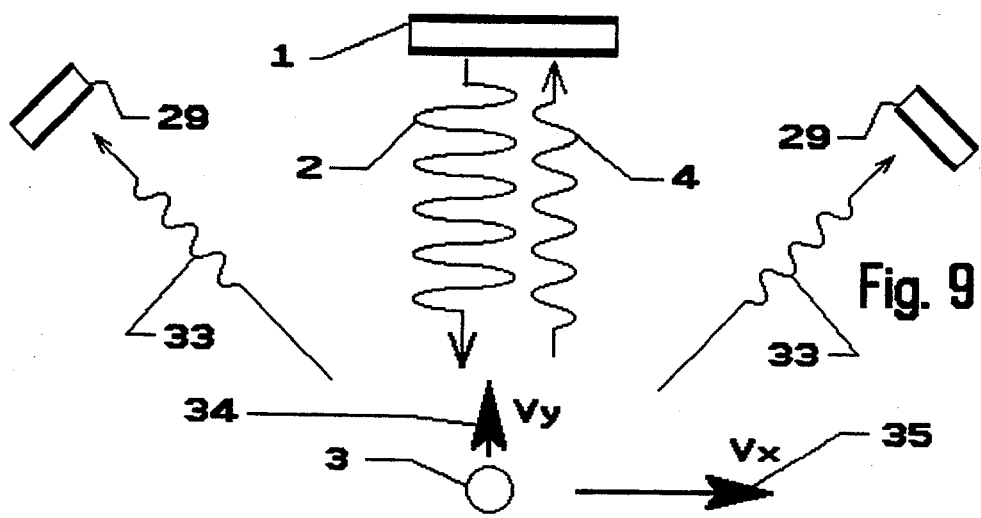

FIG. 9 is a diagrammatic representation of the operation of an ultrasonic Doppler medical device transmitting an ultrasonic pulse into a patient's body and selected components of the resulting scattered ultrasound headed toward the receiving transducers.

Figure 10:
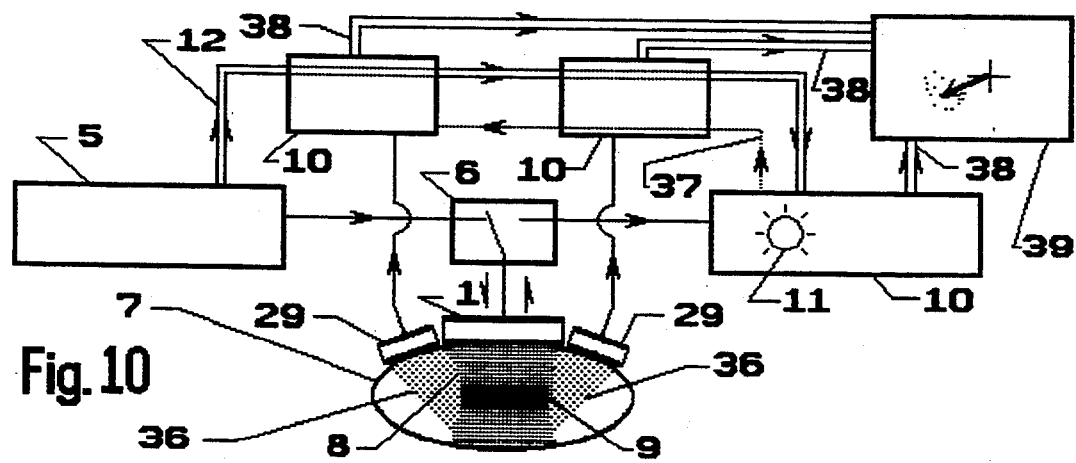

FIG. 10 is a schematic block circuit diagram of the ultrasonic vector Doppler device operating according to the diagram of FIG. 9 generating the pulse and receiving and processing the selected echoes.

Figure 11:
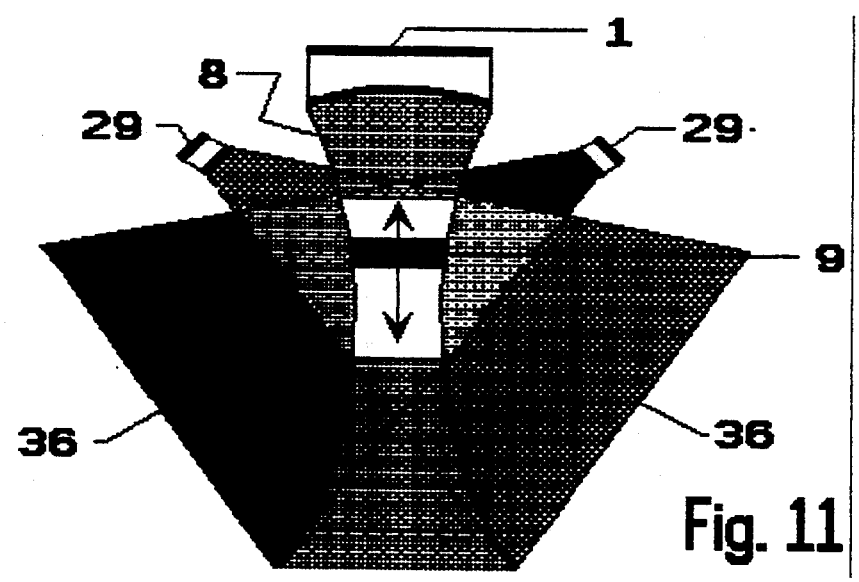

FIG. 11 is a diagram of the overlapping beam patterns of the transmitting and receiving ultrasound transducers shown in FIG. 10.

Figure 12:
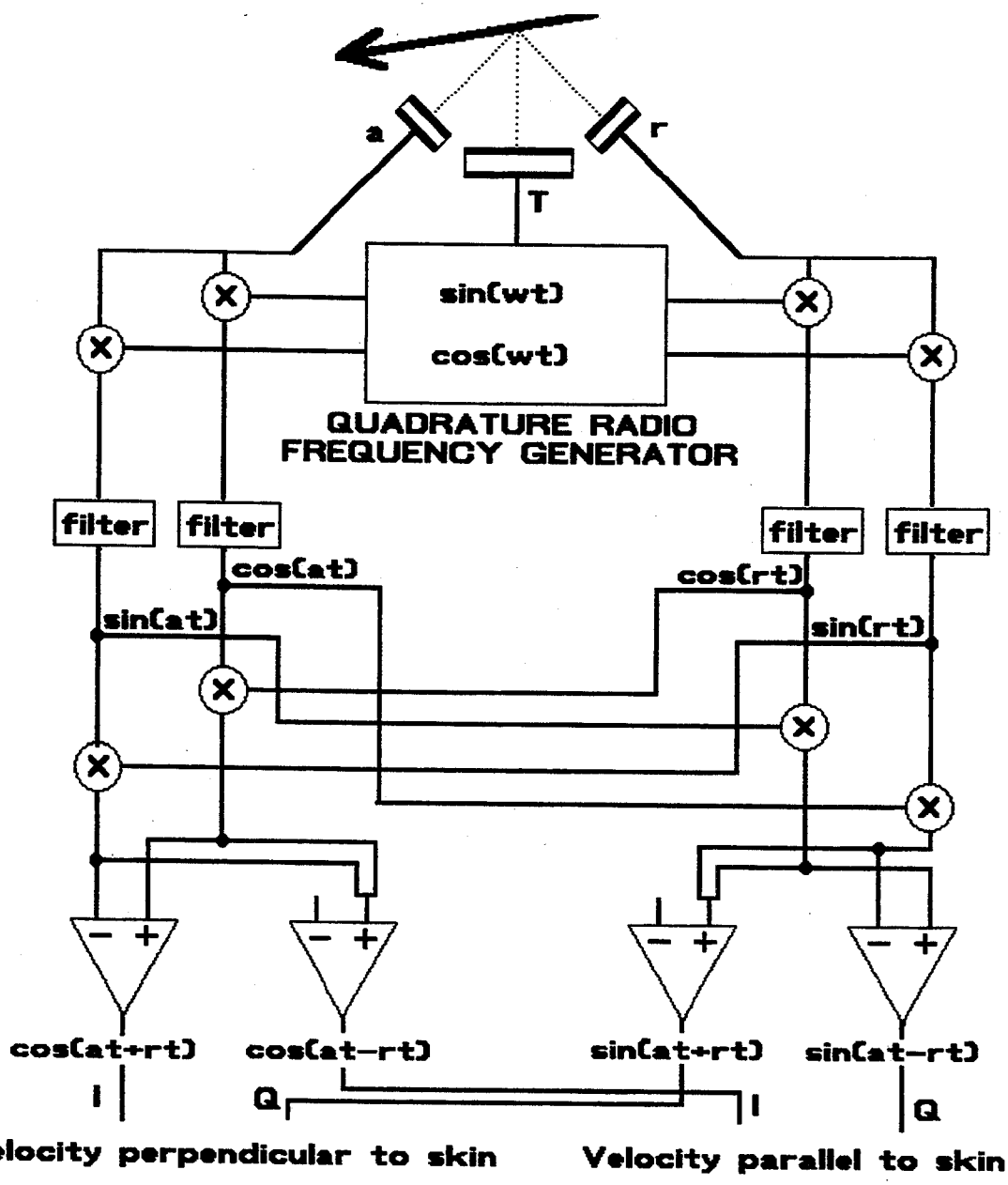

FIG. 12 is a schematic diagram of the circuit used for processing the echoes received by the receiving transducers to obtain the magnitude and orientation of a single blood velocity vector by backprojection as illustrated by FIG. 10.

Figure 13:
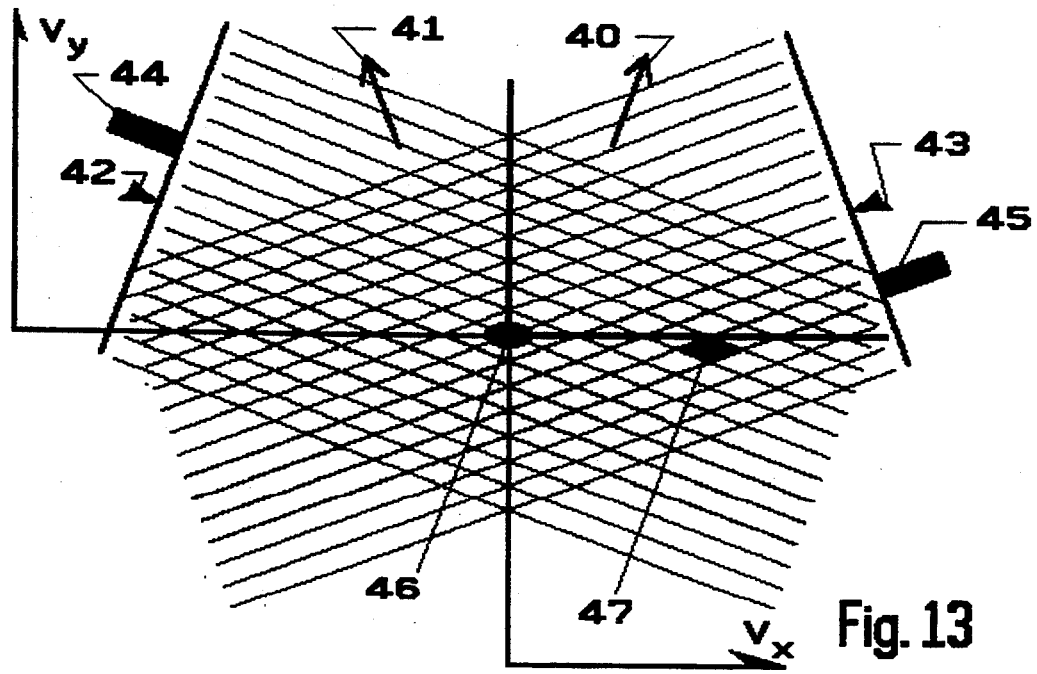

FIG. 13 is a diagram representing a velocity plane with the Doppler frequency signals received by the two separate receiving transducers shown in FIG. 10 as they are back projected to determine the orientation and magnitude of a single two-dimensional blood velocity vector that causes the pair of Doppler signals.

Figure 14:
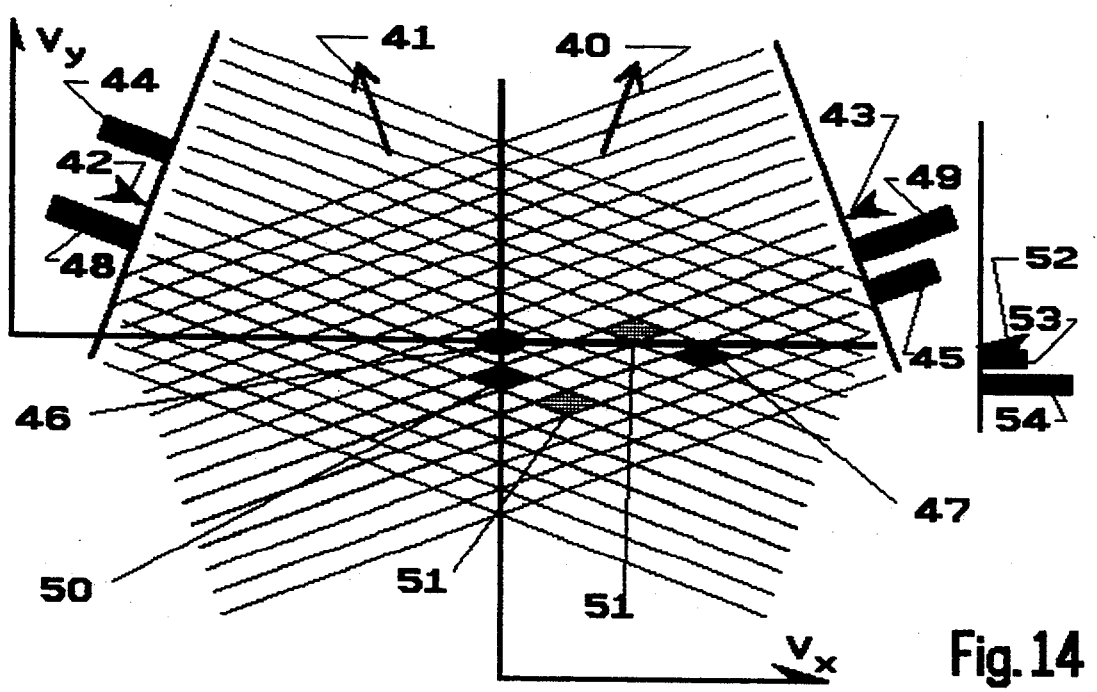

FIG. 14 is a diagram representing a velocity plane with the Doppler frequency signals observed from three separate receiving transducers as they are back-projected to determine the separate headings and magnitudes in two dimensions of the blood velocity vector that caused one pair of Doppler signals and the arterial wall velocity vector that caused the other pair of Doppler signals.

Figure 15A:
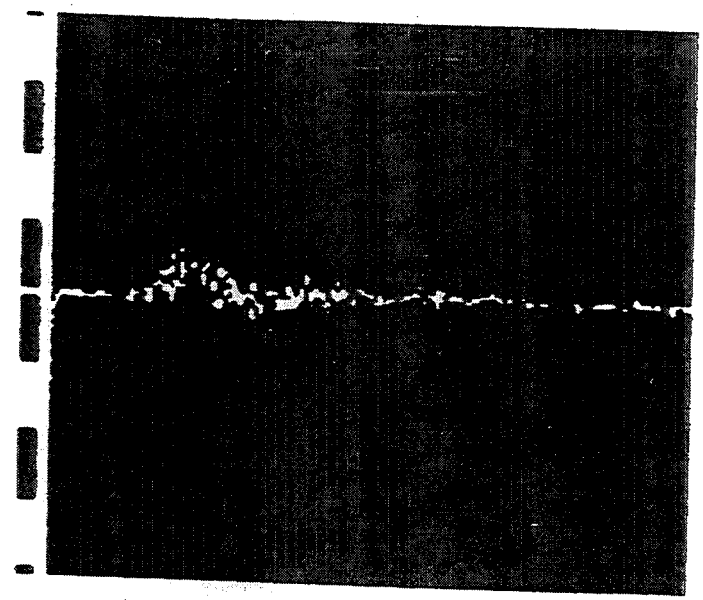

FIG. 15A is a video display of a spectral waveform showing the projected component perpendicular to the skin of blood velocity versus time. The waveform was obtained using the vector Doppler device shown in FIG. 12 on a human common carotid artery through the skin of the neck.

Figure 15B:
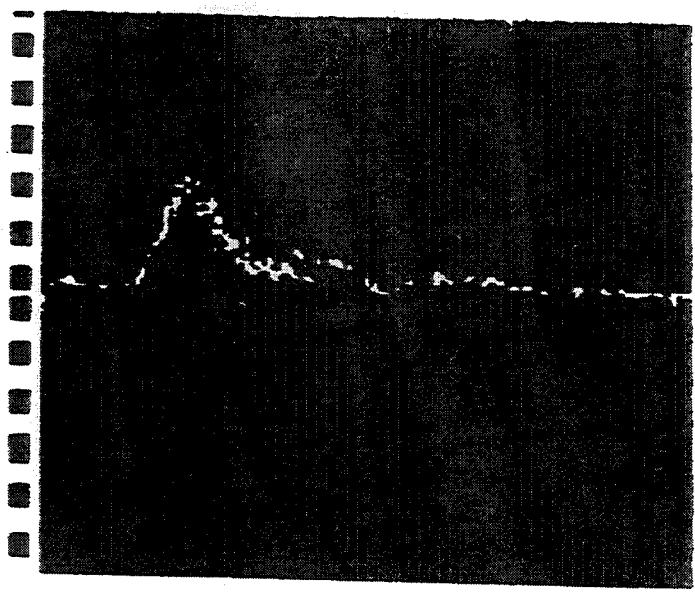

FIG. 15B is a video display of a spectral waveform showing the projected component parallel to the skin of blood velocity versus time. The waveform was obtained using the vector Doppler device shown in FIG. 12 on a human common carotid artery through the skin of the neck.

Figure 16A:

FIG. 16A is a waveform of the magnitude of a blood velocity vector obtained using the vector Doppler device shown in FIG. 12 on a human common carotid artery through the skin of the neck.

Figure 16B:
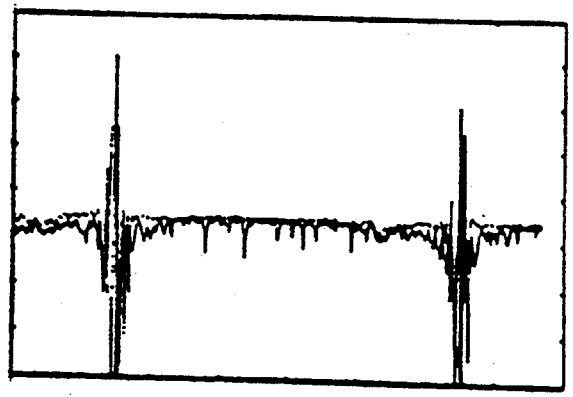

FIG. 16B is a waveform of the angle of a blood velocity vector obtained using the vector Doppler device shown in FIG. 12 on a human common carotid artery through the skin of the neck.

Figure 17:
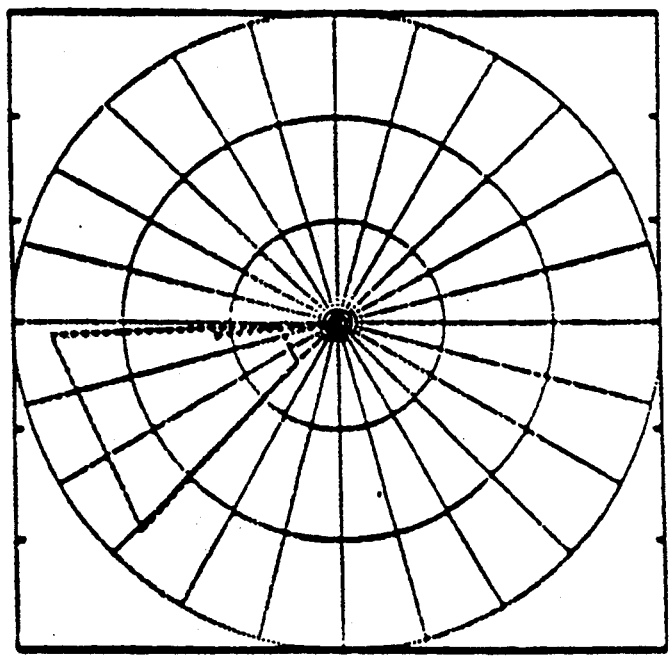
Figure 1B:
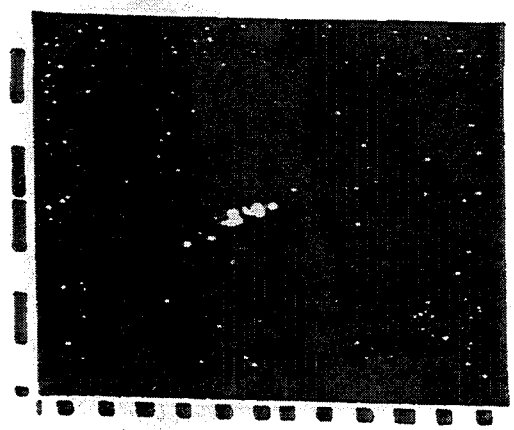

FIG. 17 is a polar coordinate display of a velocity vector heading and magnitude at one moment in time, with a quadrilateral showing the statistical confidence interval for the magnitude and heading of this measurement obtained using the vector Doppler device shown in FIG. 12 on a human common carotid artery through the skin of the neck.

FIG. 18 is a polar coordinate video display of the 128 terminations of the blood velocity vectors present at different times during a complete cardiac cycle obtained using the vector Doppler device shown in FIG. 12 on a human common carotid artery through the skin of the neck.

Figure 19:
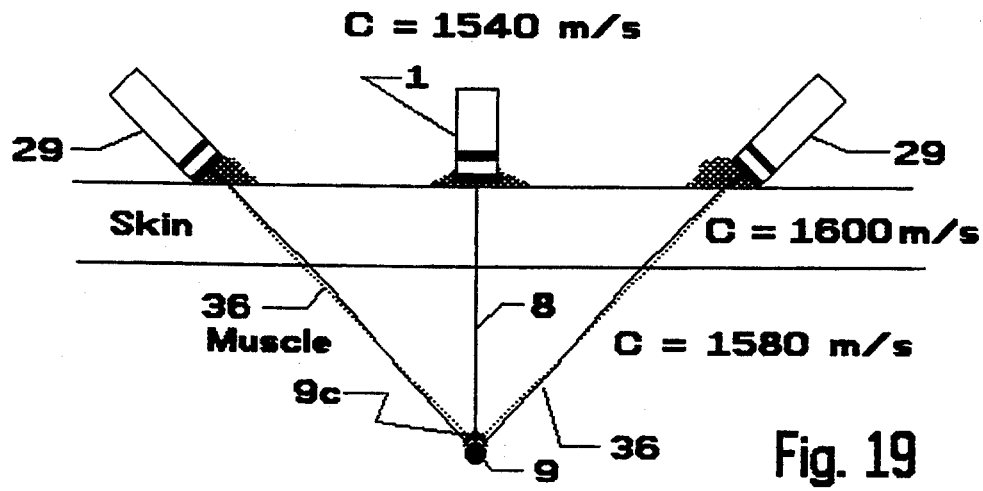

FIG. 19 is a diagram representing the error in sample volume location and angle which results from using a set of vector Doppler transducers including one transmitter and two receivers through skin and muscle.

Figure 20:
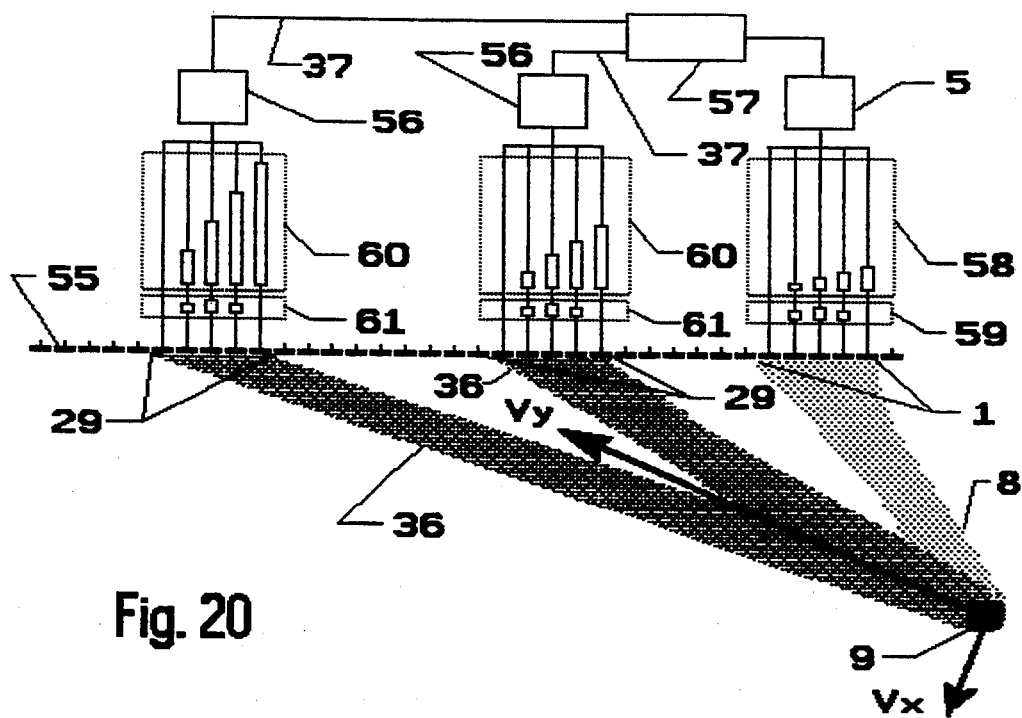

FIG. 20 is a diagram of a linear array scanhead configured for use with a vector Doppler.

Figure 21:
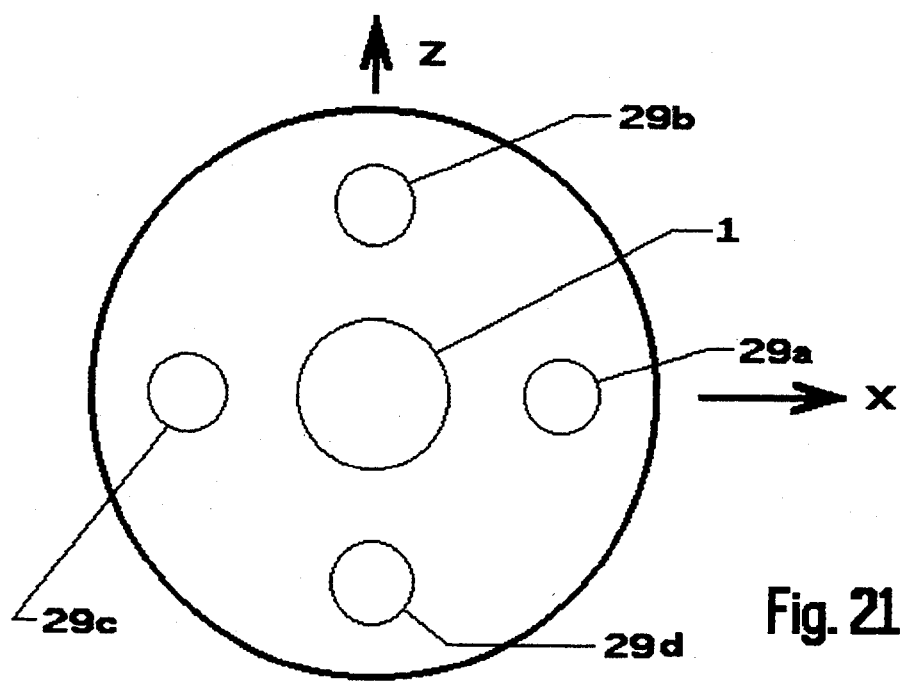

FIG. 21 is a diagrammatic plan of a scanhead having ultrasound transducers for a three-dimensional vector Doppler.

Figure 22:
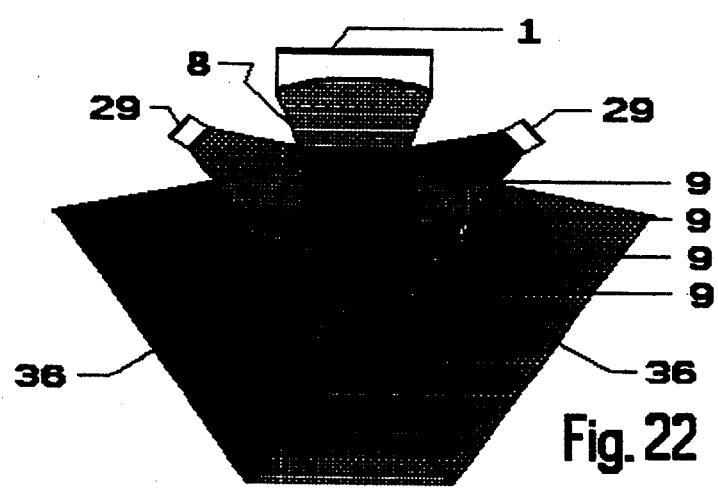

FIG. 22 is a diagram of the overlapping beam patterns of the transmitting and receiving ultrasound transducers shown in FIG. 11 with multiple receiver gates simultaneously active.

FIG. 23 is a diagram of two vector Doppler sample volumes adjacent in depth with the velocity components shown in preparation for the computation of shear rates and turbulent eddy size.

FIG. 24 is a diagram of a linear array scanhead examining a blood vessel at the point of a laminar flow convergence into a region of stenosis, and a region of normal laminar helical flow proximal to the stenosis.

DETAILED DESCRIPTION

The ultrasonic vector Doppler medical device of the present invention is designed to acquire 2-dimensional or 3-dimensional blood velocity vector information from the heart, arteries or veins of human patients:
1) in a way that permits the use of a high pulse repetition frequency to avoid aliasing,
2) in a way that permits the simultaneous acquisition of data from multiple sample volumes along a single ultrasound transmit beam,
3) in a way that is easily implemented on current linear transducer arrays used for transcutaneous or intracavity Doppler ultrasound,
4) in a way that can be used to scan a plane or region of body tissue with a sequence of ultrasound transmit pulses as does current color flow imaging,
5) in a way that permits the measurement of hemodynamic shear rates along the transmitted ultrasound beam, and
6) in a way that permits the separation of multiple velocity vectors in the sample volume on the basis of heading in addition to the conventional basis of the magnitude of one velocity component.

Such a device has a single pulsed ultrasound transmitting transducer and multiple ultrasound receiving transducers connected to range-gated phase demodulating receivers so that various combinations of phase difference changes are used to isolate, measure and properly combine the components of the blood velocities present in the body and to display such velocity components as diagnostically useful images on a video display.

The device utilizes a conventional pulsed Doppler transducer 1 shown in FIG. 9, applied to the body surface at any location from which the ultrasound waves can be directed along the line of one or more sample volumes where the velocities are to be measured. The transmitted pulse of ultrasound 2 is scattered in all headings by clusters of erythrocytes in the sample volume 3. Echoes 4 which are backscattered toward the Doppler transducer 1 can be received by it or by a separate receiving transducer adjacent to the transmitting transducer. Echoes scattered along other paths 33 are received by two receiving transducers 29 which may be located on opposite sides of the transmitting transducer. The quadrature sum of the two Doppler shifted frequencies received by the two receiving transducers 29 is proportional to the velocity component Vy parallel to the bisector 34 of the angle having the sample volume 3 as its vertex and having its arms passing through the two independent receiving transducers respectively. If the receiving transducers are located at opposite sides of the transmitting transducer and at equal distances from it, the bisector 34 of the receiver angle will coincide with the beam of the transmitted pulses 2. The quadrature difference between two such Doppler shifted frequencies is proportional to the velocity component Vx parallel to line 35 which is in the plane of the receiver location angle and perpendicular to the angle bisector 34.

A vector Doppler instrument shown in FIG. 10 has a conventional ultrasonic Doppler pulse generator 5 with its pulse directed through a transmit-receive switch 6 to a pulsed Doppler transmitting transducer 1 in contact with the skin of a patient's body 7. A portion of the transmitted ultrasound beam 8 is scattered by clusters of erythrocytes in the sample volume 9 sending echoes to the receiving transducers 29 spaced laterally at opposite sides of the transmitting transducer as well as back to the transmitting transducer 1 which also serves as a receiver. Echo signals received by the receiving transducers 29 are routed to the receivers 10 where the portion of the echoes returning from the sample volume are selected by the range gate 11 which triggers the receivers with a control signal 37 at the appropriate time when the echoes from the depth of the sample volume are expected.

The selected echoes from the sample volume are quadrature phase demodulated using a quadrature reference 12 from the transmitter. Quadrature signals from each of the receivers 38 are combined in the vector processor 39 for velocity vector display on the video image screen.

In a working vector Doppler medical device, the receiving transducers 29 had small apertures and, as shown in FIG. 11, were not focused so that the beam patterns 36 were wide permitting the depth of the sample volume 9 to be selected within a range along the transmitted ultrasound beam defined by the mutual overlap of the transmitted beam pattern 8 and the received ultrasound beam patterns 36. The system could be operated as a single gate vector Doppler with the depth of the gate adjustable or as a multigate vector Doppler permitting simultaneous acquisition of data from several depths. If multiple sample volumes are selected from the same transmit pulse by a series of range gates in conjunction with focused receivers, the heading and focus of the receiving transducers can be adjusted electronically (using electronic delay lines) several times over a period of 75 microseconds during which the echoes arrive from successively greater depths. Improved signal-to-noise can be achieved by focusing the receiving transducers at the sample volume of interest.

Determination of the magnitude and angle of a single two-dimensional velocity vector has been accomplished with the circuitry shown in FIG. 12. The velocities in the sample volume can be displayed on a two-dimensional velocity plane shown in FIG. 13. The orientation of the view of the right receiving transducer 29 (FIGS. 9 & 10) is indicated by the vector 40; this vector is parallel to the bisector of the angle having its vertex at the sample volume 9 (FIG. 10) and arms passing through the transmitting transducer 1 and right receiving transducer 29. The orientation of the view of the left receiving transducer 29 (FIGS. 9 & 10) is indicated by the vector 41; this vector is parallel to the bisector of the angle having its vertex at the sample volume 9 (FIG. 10) and arms passing through the transmitting transducer 1 and left receiving transducer 29.

The frequency spectrum from the right transducer has an origin 42 on the velocity plane with the frequency axis parallel to the view from the right transducer 40. The frequency spectrum from the left transducer has an origin 43 on the velocity plane with the frequency axis parallel to the view from the left transducer 41.

The Doppler shifted frequency peak 44 from the right receiving transducer is shown on the frequency axis for the right receiving transducer with origin 42 and the Doppler shifted frequency peak 45 from the left receiving transducer is shown on the frequency axes for the left receiving transducer with origin 43. The origin 46 of the velocity plane is located at the intersection of the projection of the origin 42 of the right transducer spectrum extended perpendicular to the frequency axis for the right transducer with the projection of the origin 43 of the left transducer spectrum extended perpendicular to the frequency axis for the left transducer. The origin of the velocity plane is also the origin of any velocity vectors on that plane. The termination 47 of the velocity vector is at the intersection of the projection of the Doppler frequency peak 44 from the right transducer with the projection of the Doppler frequency peak 45 from the left transducer. The true (two-dimensional) velocity magnitude is indicated by the scaled distance between the origin 46 and the termination 47 of the velocity vector and the heading along is the line connecting the origin 46 and termination 47. Any desired component of the velocity including Vx or Vy can be derived from the velocity vector extending from the origin 46 to the termination 47.

If the sample volume contains a second velocity vector in addition to the first as shown in FIG. 14, the additional vector will contribute an additional frequency peak 48 on the right transducer frequency spectrum and an additional frequency peak 49 on the left transducer frequency spectrum. The intersection of frequency peaks 44 and 45 from the first velocity vector will still result in the correct vector termination 47; the intersection of frequencies 48 and 49 from the second velocity vector will result in the correct vector termination 50.

In this example, blood flow in the boundary layer near the arterial wall is shown as one vector extending from the origin 46 to the termination 47, the motion of the arterial wall is shown as the other extending from the origin 46 to the termination 50. A conventional Doppler system, which has only a single receiving transducer, would only obtain the frequency spectrum from one view 41 yielding two velocity signals: 49 which has a large magnitude and represents wall motion and 45 which has a small magnitude and represents blood flow. Because the two are close in frequency and the wall signal is greater, properly rejecting the wall signal and selecting the blood velocity signal for display is difficult. Usually all low velocity signals are rejected including both blood velocity and wall signals. Thus, boundary layer velocities cannot be studied. Using the vector Doppler system of the present invention, the two signals are widely separated by heading on the two dimensional velocity plane (FIG. 14), permitting easy separation of the signals for display.

In addition to the two correct velocity vectors, two undesired intersections will also be present, arising from mathematical cross products during the determination of the desired intersections, the intersection of 44 with 49 at 51 and the intersection of 45 with 48 at 51'.

The undesired cross products will be rejected by backprojection methods. Such undesired intersections have special properties which can be used to reject them. The locations of the intersections form a parallelogram 50, 51', 47, 51 with the undesired intersections 51, 51' on opposite corners. The strengths of the undesired intersections are equal; if the strengths of the desired intersections are not equal, one desired intersection will be the largest of the four, the other desired intersection will be the smallest.

Confirmation of the identity of the correct intersections can be achieved by using the Doppler frequencies 53 and 54 obtained from the Doppler frequency spectrum acquired by a third receiving transducer having an origin 52 and directed along the bisector of the angle between the other receivers and having its apex at the sample volume. The transmitting transducer 1 (FIGS. 9, 10, 11) may serve as the third receiving transducer. By projecting the Doppler frequency peak 54 onto the velocity plane, the velocity vector termination 50 is confirmed as the common intersection of projected frequencies 48, 49 and 54, all of which have relatively greater Doppler echo strengths. By projecting the Doppler frequency peak 53 onto the velocity plane, the velocity vector termination 47 is confirmed as the common intersection of projected frequencies 44, 45 and 53, all of which have relatively smaller Doppler echo strengths. Rejection of undesired intersections 51 and 51' is confirmed because no corresponding frequencies appear on the spectrum of the third receiving transducer. Thus, the vector terminations can be identified as common intersections of projections of one frequency from each of the frequency spectra from each of the receiving transducers, with the additional property of similar strengths from each spectrum; 48, 49, and 53 are of similar magnitude; 44, 45, and 53 are of similar magnitude.

The display of multidimensional information (X, Y and Z components of velocity varying in time t and varying from position to position of the sample volume x, y, and z) on a two-dimensional plane is a challenge. Time versus Velocity in each of two perpendicular headings can be shown as a pair of spectral waveforms as shown in the video displays of FIGS. 15A and 15B. This pair of tracings was simultaneously recorded from a sample volume in a human common carotid artery. The video images were created by taking a time series of velocity vector components from a time series of velocity planes as shown in FIG. 13. FIG. 15A is a view of the velocity vector components Vy from the left side of FIG. 13 of a time series (or stack) of velocity planes like FIG. 13; FIG. 15B is a view of the velocity vector components Vx from the below of FIG. 13 of a time series (or stack) of velocity planes like FIG. 13

The waveform of the blood velocity component perpendicular to the skin is shown in FIG. 15A; upward displacement of the tracing represents flow away from the ultrasound transducer. The waveform of the blood velocity component parallel to the skin is shown in FIG. 15B. The systolic peak on the left of FIG. 15B, is aligned in time with a similar small peak on FIG. 15A; this indicates that in systole, the blood velocity vector heading is tilted downward with respect to the skin.

The instantaneous velocity waveforms in the video displays of FIGS. 16A and 16B show velocity magnitude versus time (FIG. 16A) and angle versus time (FIG. 16B) from the common carotid artery. The waveforms are also derived from a time series of sequential velocity planes. The angle of the vector (FIG. 16B) is nearly constant at 160 degrees. As expected, the angle becomes uncertain when the velocity magnitude is near zero.

The concept behind the spectral waveforms in FIG. 15A and FIG. 15B is different from the concept behind the instantaneous velocity waveform in FIG. 16A and FIG. 16B. In the spectral waveforms, the underlying concept is that at any moment in time (a period of 10 milliseconds), multiple velocities may be simultaneously present in the Doppler sample volume; each spectrum that makes up the spectral waveforms (FIG. 15A and FIG. 15B) shows all of the velocities present. In the instantaneous velocity waveform (FIGS. 16A and 16B), the underlying assumption is that only a single velocity magnitude and heading is present at any moment in time, and that value can be determined quickly. At a later time, another velocity magnitude and heading is present. The instantaneous velocity waveforms showing velocity magnitude (FIG. 16A) and angle with respect to the skin (FIG. 16B) show only one velocity for each moment in time. The difference is not important for simple, midstream, blood velocities that are parallel to the axis of the artery, but in complex situations where two or more flow streams are present simultaneously in the sample volume, the instantaneous plot fails to show the detail that proper diagnosis requires. Therefore spectral projection displays, based on projection analyses as shown in FIG. 14, offer a diagnostic advantage over instantaneous frequency analysis methods.

The video display of FIG. 17 shows an instantaneous polar plot with magnitude, angle and confidence region (shown as a quadrilateral) at one point in time. This video image is derived from one velocity plane image such as FIG. 13. The confidence region provides the examiner with an impression of the variance of the velocity. The angle variance and the magnitude variance are independent. Each contributes to an understanding of the disturbances in the flow. However, the diagnostic utility of these values is not, as yet, clear.

FIG. 18 shows a trajectory of the vector termination with time in the cardiac cycle in the distal common carotid artery, just upstream from the bifurcation forming the internal carotid artery and the external carotid artery. This display is a cumulative superposition of velocity plane data such as FIG. 13. This display is generated in real time providing a kinetic image. During the examination, the screen display is initiated; each 10 ms(millisecond), a new point is added to the screen. Each point on the display represents a different 10 ms period in time during the cardiac cycle. All of the points are located to the left and below the central origin showing that the velocity vectors representing each time period in the cardiac cycle, are all angled down and to the left. The trajectory of the points demonstrates that in this volunteer patient, the systolic arterial flow is first directed from the common carotid artery into the external carotid artery, then about 100 milliseconds later, the flow is redirected into the internal carotid artery. This kind of detail about the changing direction of velocity vectors has never before been possible with ultrasonic devices.

The use of a single transmitting transducer serves to minimize the refractive separation of the sample volumes which appeared in the device by Daigle (FIG. 5). As shown in FIG. 19, by using a single transmitting transducer 1 the coincidence of the sample volumes 9c viewed by different receivers 29 is maximized because all sample volumes must lie on the focused, transmitted ultrasound beam pattern 8.

The vector Doppler system may be implemented by use of a standard ultrasonic linear array scanhead as shown in FIG. 20. A portion of the phased linear array can be used as a Doppler transmitting transducer 1 by sending a 5 cycle Doppler ultrasound pulse from the ultrasound generator 5 to a group of elements in the array. The transmitted beam pattern can be steered to any angle in the image plane by a set of electronic delay lines 58 and focused into an ultrasound beam pattern 8 which is directed toward the sample volume 9 by a set of focusing delay lines 59. Echoes returning along beam paths 36 headed toward groups of elements in the array 29 connected to act as receiving transducers can be processed by the vector Doppler receivers 56.

A master timing circuit 57 is used to trigger the Doppler receivers 56 via trigger lines 37 so that each receiver 56 is activated at the proper time to receive the echoes from the sample volume 9. Each receiving transducer array 29 is directed toward the sample volume by electronic delay lines 60 which steer the beam pattern in the direction of the sample volume. In addition, each receiving transducer array 29 is focused on the sample volume 9 by focusing delay lines 61. The quadrature difference between the Doppler shifted frequencies received by the two receivers is proportional to the velocity component Vx perpendicular to the bisector of the angle between the receiver beam patterns 36; the quadrature sum of the Doppler shifted frequencies received by the two receivers is proportional to the velocity component Vy along the bisector of the angle between the receiver beam patterns 36.

Three mutually perpendicular components of each velocity vector in the sample volume can be conveniently obtained by using a scanhead with five ultrasound transducers on the skin as shown in FIG. 21. The central transducer 1 may be used for both transmitting the Doppler ultrasound pulse and receiving Doppler ultrasound echoes. Four receiving transducers 29a, 29b, 29c and 29d are located in a circle. Receiving transducers can be formed in opposite pairs: receivers 29a and 29c being in a line at an angle to a line joining receiver 29b and 28d; members of each pair are on diametrically opposite sides of the central transducer 1. Processing the echoes received by the central transducer gives the velocity component which is perpendicular to the skin (the Y heading) of each blood velocity vector; processing the echoes from the pair of transducers 29a and 29c to produce the quadrature difference frequency provides the velocity component with the X heading of each blood velocity vector; processing the echoes from the other pair of transducers 29b and 29d to produce the quadrature difference frequency, provides the velocity component in the Z heading of each blood velocity vector.

Additional possible vector components along the Y heading are obtained by processing the echoes from one pair of transducers 29a and 29c to produce the quadrature sum frequency and by processing the echoes from the other pair of transducers 29b and 29d to produce the quadrature sum frequency. Three dimensional back projection methods can be used to eliminate undesired intersections in the presence of multiple velocity vectors as shown in FIG. 14.

Of course, any number or arrangement of receivers could be located on the skin and used simultaneously, each obtaining another projection of the velocity vector using the echoes from a set of transmit pulses from a single common transmitting transducer. These additional receiving transducers might be helpful in very complex flow conditions. In addition to complex velocity combinations, vibrations of solid tissue in the audible range (arterial bruits, or heart murmurs, commonly heard by physicians through a stethoscope) are processed as Doppler velocity signals representing blood flow. The velocity signals and the bruit signals can be easily separated because they differ in two ways:
1) The Doppler signals are frequency shifted ultrasound and therefore become single sideband signals on demodulation; the bruit signals are audio frequency and therefore become double sideband signals on demodulation.
2) The Doppler signals are echoes from blood and are therefore weak; the bruit signals are echoes from solid tissue and are therefore strong. When bruit signals pass through a Doppler processor, the double sideband signals have multiple harmonics.

These two differences can be used to differentiate bruit signals from Doppler signals.

Using the methods above, measurements of velocity magnitude and heading can be performed simultaneously from a series of Doppler sample volumes 9 (FIG. 22) located along the axis of the beam pattern 8 of the transmitting transducer 1 where it intersects the beam patterns from the receiving transducers 29. Velocity magnitude data or heading data from all of the sample volumes along the transmitting transducer axis can be shown on a video display as lateral displacements of a vertical line; the vertical dimension represents depth, lateral displacements represent velocity magnitude, a display similar to FIG $B_2$ as done by Hoeks (R. S. Reneman). As an alternative, a video display can be created in which the vertical dimension represents depth and different values of velocity magnitude are shown as different colors (M. K. Eyer).

In addition to showing the velocity values directly, the derivative of velocity with depth can be computed within the display processor 39 (FIG. 10) by taking the difference between the velocity in a sample volume at one depth y1 (FIG. 23) and the velocity in a sample volume at another depth y2 and dividing the difference by the distance d between the sample volumes. The resultant hemodynamic shear rate, combined with the fluid viscosity can be used to predict the rate of energy loss in the volume bounded by the two sample volumes. The rate of energy loss in a volume is related to the pressure drop along the direction of flow, and can be used to identify arterial stenoses that are responsible for distal tissue ischemia.

A second parameter can be measured using the velocity data from a series of sample volumes: the turbulent eddy size. The correlation in time between the velocity in one sample volume with the velocity in another can be computed. If the correlation is high, the two sample volumes are located within the same eddy; if the correlation is low, the sample volumes are in different eddies. By determining the correlation as a function of distance between sample volumes, the eddy size can be defined as the distance when the correlation drops below a certain limit. Inverse eddy size can be displayed on a video screen as a measure of turbulent intensity.

A two-dimensional vector Doppler system, applied to the clinical problems of the entry to a stenosis and of helical flow, as shown in FIG. 24, can reveal new information about the nature of the flow and prevent inaccurate measurements and incorrect diagnoses. At one location, the entry to a stenosis is examined and the anomalous flow reversal shown in FIG. $B_2$ is correctly evaluated and displayed differentiating the change in angle from the change in flow direction using the vector Doppler 55a & 56a (FIG. 24). At the other location, helical flow is examined and the anomalous increase in velocity resulting from conventional Doppler examinations as shown in FIG. $D_2$ is correctly evaluated and displayed so that the examiner can select the diameter plane by seeking the examination plane which results in a heading angle display 56b on the vector Doppler indicating angles parallel to the vessel axis (FIG. 24).

The ultrasonic velocity signals from the region of the stenosis entry are received by transducers 29a and displayed as velocity magnitude versus depth 55a and heading angle versus depth 56a. The negative heading angle at the superficial side of the vessel, the high velocity magnitude at the center and the positive heading angle at the deep side of the vessel, confirm the smooth laminar entry to a stenosis.

The ultrasonic velocity signals from a diameter of the artery in the region of normal helical flow are received by the transducers 29b and displayed on a video screen as velocity magnitude versus depth 55b and heading angle versus depth 56b. In the plane containing both the vessel axis and the vertical diameter, the component of the heading angle is zero (parallel to the vessel axis) at all depths, and the magnitudes of the velocity in that plane are nearly uniform in the central half of the vessel. In contrast, angling the transducer array 1b, 29b to displace the sample volumes to a location that is slightly in front of the plane of the drawing will cause the sample volumes to intersect the upward heading side of the helical flow pattern. In that case, a maximum in the velocity magnitude versus depth display 55b' is seen at a central depth, but the heading angle 56b' also assumes positive values where the tilt of the vector is the greatest.

As long as the plane of the vector Doppler examination is parallel to the vessel axis, the velocity component parallel to the axis can be determined by multiplying the velocity magnitude by the cosine of the heading angle. That result, if integrated by the display processor across the vessel cross sectional area will give an accurate measurement of volumetric flow rate.

A two-dimensional vector Doppler examination can be used to determine the maximum velocity magnitude in the vessel for use in determining the kinetic energy as used in the Bernoulli equation. The technique is to rotate the plane of the scanhead around an axis perpendicular to the skin while observing the velocity magnitude versus depth. At the angle where the magnitude is greatest, the examination plane is aligned with the vector and the magnitude displayed is the true magnitude. If a three-dimensional vector Doppler is used, the true magnitude is always available for display.

In the echocardiographic examination of the aortic valve from the esophagus using trans-esophageal echocardiography, an excellent view of the aortic valve is obtained because the distance to the valve is small and the angle to the valve axis is nearly 90 degrees. Unfortunately, using currently available ultrasonic velocity systems, the blood velocity through the valve cannot be determined during that examination because the ultrasound scan lines are perpendicular to the principal velocity vector through the aortic valve. If the trans-esophageal scanhead were fitted with three-dimensional vector Doppler transducers, the heading and magnitude of the principal velocity vector through the aortic valve could be studied during the examination, as well as changes in the velocity vectors with position in the valve orifice and with time in the cardiac cycle.

Two dimensional and three dimensional velocity data characterizing all of the blood velocities in each sample volume in a flow field, as is provided by the Vector Doppler, are superior to the single component data provided by conventional Doppler systems for several reasons:
1) Two-dimensional color Vector velocity data permits the correct identification of forward and reverse flow in curved and branched arteries, avoiding common errors in diagnosis with color Doppler systems.
2) Vector velocity data permits the correct computation of volumetric flow rate through an artery using any angle of view to the axis of the artery, so long as the correct arterial diameter can be measured.
3) Vector velocity data permits the correct computation of the Bernoulli pressure depression in arterial stenoses.
4) Using back projection, if multiple velocity vectors are simultaneously present in the selected sample volume, the separate vectors can be resolved on the basis of heading as well as magnitude, and then selected for individual display.
5) Slow blood velocities near the wall of an artery where both the blood and the wall are in motion can be studied. When using a conventional Doppler, in the process of rejecting the strong echoes from the wall, all weak echoes containing information about the marginal boundary layer blood velocities are lost. Using heading information from the vector Doppler, marginal boundary layer Doppler signals can be preserved.
6) New information about turbulent flow can be measured including the rate of energy loss and the turbulent eddy size.

The benefit of vector Doppler information can be realized, using linear array and phased array scanheads of conventional design, with no sacrifice in pulse repetition frequency. Therefore, the implementation of the vector Doppler methods is easy; in addition, there is no tradeoff in instrument performance. Only a modest increase in the complexity of instruments is required to implement a 2-dimensional vector Doppler system on existing ultrasound instruments.

DEFINITIONS OF TERMS

Acoustic Impedance: The ratio of the change in molecular velocity to the change in tissue pressure as a sound wave passes through a body tissue. According to the theory of waves, whenever a wave encounters a boundary between a material having one impedance and a material having a different impedance, a portion of the wave energy is transmitted and a portion of the wave energy is reflected.

Algorithm: A set of steps to convert data from a signal source into data which represents the signal for display.

Aliasing: When an image of data with a limited range must display data outside that range, the data is correctly shown in an incorrect location; a 15 KHz Doppler signal will be shown on a display having a range $-4$ KHz to $+12$ KHz at the location indicating $-1$ KHz ($15-12=+3$, $-4+3=-1$). The quadrature pair of Doppler signals in a directional Doppler device permits "negative" as well as "positive" frequencies to be processed and displayed.

Amplitude Demodulation: The extraction of information from an ultrasound signal based on the strength or amplitude of that signal.

Arterial Doppler Signal: The audible sound from a Doppler device with the sample volume monitoring the blood velocity in an artery.

Backprojection: Determining the location of one or more objects in multidimensional space by using the locations of images of the objects in multiple projected views of known relationship to the multidimensional space; in this case, the objects are the terminations of velocity vectors in three-dimensional space, the relationship of each view to the space is determined by the locations of transducers with respect to the sample volume where the velocity vectors are present. These techniques are sometimes called reconstruction or tomography.

Beam Pattern: The region of tissue that receives insonication from a transmitting ultrasound transducer; the region of tissue from which a receiving transducer is sensitive to ultrasound. For a transducer serving to both transmit and receive (a transceiver), the region of insonication and of sensitivity are coincident. The region extends for a distance in front of the transducer, usually converging on a focus and then expanding beyond. The region is not sharply defined; portions of the region have greater or lesser transmitting intensity and receiving sensitivity. Although the beam pattern is considered to be pointed along a single path, sidelobes are usually unavoidable.

Bidirectional: see directional.

Biphasic: The presence of two sounds in an arterial Doppler signal during the systolic time period of each cardiac cycle; often the first sound is associated with forward flow (away from the heart) and the second with reverse flow, although the two sounds could both represent forward flow separated by a dicrotic wave during systole (see monophasic, triphasic).

Cell: An element of living tissue of size ranging from 0.002 mm to 1 mm enclosed in a membrane. The size of red blood cells (erythrocytes) is 0.008 mm in diameter; erythrocytes are unusual cells as they contain no nucleus.

Closing Speed: The speed at which a cluster of erythrocytes approaches the active Doppler ultrasound transducer along the common path of the transmitted ultrasound beam and returning ultrasound echoes.

Component: see Projection.

Continuous Wave (CW) Doppler: A Doppler method in which one transducer is used for continuously transmitting ultrasound into tissue and an adjacent transducer is used for continuously receiving the ultrasound echoes from tissue. Such a Doppler is sensitive to blood velocities at all depths in tissue which are within the ultrasound beam; but the depth of the moving blood cannot be determined.

Depth Resolution: A distance measured in units of millimeters which is the minimum separation distance in the depth dimension between two echogenic objects that results in separate images of the objects in the display.

Diastole, Diastolic: Arterial diastole is the period between contractions of the left ventricle of the heart when the blood is not ejected through the aortic valve. During this period the blood velocities and pressures in peripheral arteries are low.

Dicrotic wave: A local Doppler frequency minimum in an arterial waveform which occurs at the end of systole.

Direction: Referring to travel along a linear path, only two directions are possible: advancing and receding. Direction suggests nothing about the heading of the path.

Directional: The ability of velocity measuring instrumentation to differentiate motion in one direction from motion in the opposite direction along a reference heading.

Distal: Farther from the heart than the point of measurement or discussion.

Doppler Frequency: An audible frequency resulting from the wave interference between the Doppler shifted frequencies of echoes returning from the Doppler sample volume and the transmitted ultrasound frequency. The transmitted ultrasound frequency of 5,000,000 Hz (5 MHz) may be combined with the Doppler shifted ultrasound echo of 5,000,440 Hz to form a Doppler frequency of 440 Hz, which is in the audible range (below 20,000 Hz). Faster blood flow would create a greater Doppler frequency.

Doppler Pulse: see Pulse Ultrasound

Doppler Signal: The audible output of a Doppler system with frequency proportional to the closing speed of blood.

Doppler System: A transmit-echo system which uses measurements of the change of the phase of the echo compared to the transmitted ultrasound wave divided by the time between echoes to determine the speed at which reflective objects such as erythrocytes are approaching the transmitting and receiving transducers or receding from the transducers. "Doppler system" here includes time-domain velocity measurement systems.

Echo Signature: A pattern of ultrasound echo cycles that is unique to a particular number and arrangement of echogenic cells in the sample volume. Each signature is unique; therefore if the echoes from similar depths in tissue originating from different transmit pulses have identical signatures, this indicates that the same group of cells is responsible for the two signatures. The depth displacement of the echo signature between transmit pulses indicates that the cells have changed in depth in the time interval between pulses.

Echoes: Ultrasound waves that result from an ultrasound pulse transmitted into tissue becoming scattered because of changes in the acoustic impedance of the tissue. The portions of the scattered waves which travel toward an ultrasound receiving transducer are echoes.

Echogenic: The property of material resulting in the creation of strong ultrasound echoes from such materials.

Echogenicity: The extent to which a tissue material can reflect incident ultrasound toward a receiving transducer.

Endpoint Detection: In the indirect measurement of blood pressure in a blood vessel using a cuff/sphygmomanometer, after the cuff is inflated above the highest pressure in the vessel to occlude the blood flow, and during the period while the cuff is being slowly deflated, the endpoint of the measurement is the time when the return of blood flow is detected in the vessel indicating that the pressure in the cuff has fallen below the intravascular pressure.

Erythrocytes: Red blood cells.

Filter: see High Pass Filter, Low Pass Filter

Flowrate: The volume of blood passing through an artery (or vein) divided by time (units cubic centimeters/second). Flowrate is often averaged over several cardiac cycles, but may be instantaneous. It may be determined by computing the product of the component of velocity perpendicular to a surface times the elemental area of the surface, and integrating over the area of intersection of that surface with the lumen of the artery.

Heading: The angular orientation of a vector in the three spatial dimensions; often the word direction is used, but that word has a prior common usage in Doppler systems. In ship navigation, heading refers to the compass reading, the heading on a two dimensional surface. In aircraft or submarine navigation, a second value is required to indicate the third dimension of ascent or descent. In the two dimensional vector Doppler, heading may be indicated as a single angle or as a pair of directional cosine components of a unit vector. In the three dimensional vector Doppler, a pair of angle values (latitude and longitude) or three directional cosine components of a unit vector are required.

High Pass Filter: A portion of the electronic circuit of the Doppler receiver which suppresses the lowest Doppler frequencies (0 to 50 Hz). Such low frequencies probably result from motion of the arterial wall rather than from blood velocities.

Imaging: In ultrasound technology, 2-dimensional B-mode (brightness mode) imaging is the creation of a display on a screen in which the height and width dimensions on the screen correspond to the depth and lateral dimensions on a plane transecting the tissue and the brightness of each location on the screen corresponds to the strength of the echo determined by amplitude demodulation.

Imaging Pulse: See Pulse-Ultrasound.

Incompetence: Abnormal backward flow of blood through a valve of the veins or a valve of the heart. Synonyms:: Reflux, Regurgitation.

Insonication: The transmission of ultrasound through tissue.

Low Pass Filter: A portion of the electronic circuit of the Doppler receiver which suppresses the Doppler frequencies above the range of human hearing (20,000

Hz). During phase demodulation, unwanted ultrasound appear combined with the audible Doppler frequencies; the low pass filter suppresses these high ultrasound frequencies.

M-Mode (Motion-Mode) Display: A two-dimensional display on a screen designed to show the motion of cardiac structures; depth along the stationary ultrasound beam pattern is shown in the vertical dimension on the image and time is shown in the horizontal dimension. Stationary structures appear on the display as horizontal lines; moving structures appear on the display as tilted lines. Brightness of the display is proportional to tissue echogenicity. Modern instruments have display screens which show areas where blood velocity is detected as areas of color (red for flow in one direction and blue for flow in the other direction) superimposed on the M-mode image.

Manual Compression: Exerting localized pressure on the leg by hand.

Monophasic: The presence of only one sound in an arterial Doppler signal during systolic time period of each cardiac cycle; this sound is considered to represent forward flow (away from the heart), (see biphasic, tripbasic).

Multigate (Pulsed) Doppler: A pulsed Doppler method in which the Doppler shift frequencies are computed at the same time from a series of sample gates along a single ultrasound beam. Commercial systems have had 6 gates, 32 gates, 64 gates and 128 gates on a single ultrasound transmit beam.

Noninvasive: Methods which do not require penetrating the skin or other intact barriers of the body with a material object; in addition methods which do not require the penetration of body tissues with ionizing radiation. Insertion of an ultrasound scanhead in a body cavity such as the esophagus for the study of the heart, is "noninvasive".

Peripheral Artery: An artery carrying blood from the heart to the bodily tissues that is located outside the chest.

Phase Demodulation: The extraction of information from an ultrasonic wave signal based on the timing of the cycles of the wave.

PRF=Pulse Repetition Frequency: The number of pulse-echo cycles that are transmitted into tissue per second to obtain ultrasound echo data to form an ultrasound image or Doppler signal; the maximum PRF is determined by the time required for echoes to return from the deepest tissues (MaxPRF=2 * D/C, where D is the maximum tissue depth and C is the speed of ultrasound in tissue).

Processor: A device, which may be digital, analog or a combination of digital and analog, which performs a defined series of mathematical operations on a set of Doppler signals to combine the signals into a result; the mathematical operations may include addition, subtraction, multiplication, and division.

Projection: The projection of a velocity vector (which has three-dimensional properties) onto a line is accomplished by multiplying the magnitude of the velocity vector by the cosine of the angle between the velocity vector heading and the heading of the line; the resulting scaler quantity with + or − sign is the component of the velocity vector along the line of projection. The projection of a three-dimensional velocity vector onto a plane results in a vector in that plane; this vector is a component of the three-dimensional velocity vector.

Proximal: Closer to the heart than the point of measurement or discussion.

Pulsed Doppler: A pulse-ultrasound Doppler method which permits the examiner to choose a particular depth beneath the skin for the Doppler velocity measurement.

Pulse-Ultrasound: A short period of ultrasound transmission into tissue. A pulse used for imaging lasts 1 cycle (0.2 microseconds for 5 MegaHertz ultrasound). The shortest possible transmit pulse is used to assure superior depth resolution. A pulse used for Doppler lasts 1 microsecond (5 cycles for 5 MegaHertz ultrasound). The pulse contains multiple cycles to assure proper phase coherence in the echo for comparison with the reference wave during phase demodulation. A pulse used for Time-Domain velocity measurement lasts 1 cycle or 0.2 microseconds. A short pulse is used to create a unique echo signature from each configuration of cells in tissue or blood.

Quadrature Demodulation: The method of phase demodulation in which a signal is phase correlated with one reference wave of several cycles and constant amplitude to produce one result called REAL and is phase correlated with a second reference wave which differs from the first only in that the phase is delayed by one quarter cycle to produce a second result called IMAGINARY. The mathematical topic "complex algebra" deals with manipulating numbers having a REAL term and an IMAGINARY term. A complex number with the two terms can be represented by a vector on a plane. The REAL term has a value multiplied by 1. The IMAGINARY term has a value multiplied by the square root of −1, a process that cannot be done, except in the imagination. Even so, useful mathematical manipulations can be done in complex math using combinations of REAL and IMAGINARY numbers.

Real Time: The ability to display the results of analysis within milliseconds after data acquisition and to update the display at a frame rate near the flicker fusion rate of the eye (as is done in moving pictures or on television) to give the impression that the display is showing current events.

Reflux: See Incompetence.

Refraction: The bending of an ultrasound beam as it passes at an oblique angle across an interface from a material in which ultrasound waves propagate at one speed to a material in which ultrasound waves propagate at a different speed. If the interface is not flat over the intersection with the beam pattern, portions of the pattern will be bent at different angles resulting in dispersion of the beam pattern.

Regurgitation: See Incompetence.

Sample Gate: The electronic switch in the receiver which selects the depth of the sample volume. As an example, the transmitted ultrasound pulse may last 1 microsecond, a delay period of 40 microseconds will select echoes returning from a depth of 3 cm (round trip travel at an ultrasound wave speed of 0.15 cm/us in human tissue); between 40 and 41 microseconds after the transmit pulse a 1 microsecond sample of the echo will be taken by the sample gate.

Sample Volume: A volume in tissue selected as the site where velocity is to be measured. The sample volume is located within the beam pattern of the transmitting and receiving ultrasound transducers at the depth beneath the portion of the skin to which the ultrasound transducer is applied by selecting a predetermined short period after the ultrasound pulse is transmitted to sample the echo (see Sample Gate). The sample volume from a circular transducer is cylindrical with a length of approximately 0.15 cm and a diameter of approximately 0.3 cm.

Scanhead: An apparatus which contains one or more ultrasound transducers which contact the body surface. The apparatus contains means for selecting the location of the origin, the heading, and the focal characteristics for emission of the ultrasound transmit pulse and a means for selecting the locations of sensitivity, the heading and focus of the sensitivity patterns for ultrasound receiving.

Sidelobes: Portions of an ultrasound beam pattern that are pointed in directions other than the main portion of the beam pattern. Usually sidelobes are symmetrical around the central portion of the beam pattern.

Snell's Law: As a wave passes through a plane from a material in which the propagation speed is C1 to a material in which the propagation speed is C2, the angle $\phi1$ between the propagation of the incident wave and a line perpendicular to the plane is related to the angle $\phi2$ between the propagation of the transmitted wave and said line perpendicular to the plane by the expression:

$$C2*\sin(\phi1) = C1*\sin(\phi2)$$

Spectral Waveform: A set of several hundred spectra, each representing a short period in time (usually 0.01 second), arranged side by side along the abscissa with the frequency (velocity) values displayed on the ordinate and the power of each frequency indicated by the density of the gray scale at that frequency. The spacing of adjacent spectra is 1 mm permitting 1 second of time in the cardiac cycle to be represented by 100 mm along the abscissa.

Spectrum (pl. Spectra): A graphical plot showing the power of each Doppler frequency present in the Doppler signal. Often frequency is indicated on a scale along the abscissa and the power of each frequency is indicated as displacement of the tracing to align with the corresponding value of the power scale along the ordinate. In a spectral waveform, each spectrum is rotated and power shown as brightness rather than displacement.

Speed: A scalar quantity, the magnitude of the velocity.

Statistical Confidence Interval: Given the numeric value of the result of a measurement of a sample of data which is subject to statistical variability, the 95% confidence interval is the range of possible values which is expected to include 95% of the results of the measurements if the measurement is repeated a large number of times.

Symbols
* refers to the multiplication of two numbers.
/ refers to dividing left number by right number.
(X) refers to the multiplication of two signals to yield a third.

Systole, (Systolic): Arterial systole is the period during contraction of the right ventricle of the heart when the blood is ejected through the aortic valve and blood velocities and pressures in peripheral arteries are high.

Target: The region of tissue in the sample volume containing a cluster of erythrocytes or other objects which reflect and scatter ultrasound.

Time-Domain Pulse: see Pulse Ultrasound

Time-Domain Velocity Measurement: A method of measuring the speed at which a group of erythrocytes is approaching the ultrasound transducer by measuring the difference in time between pulse transmission and reception of the echo signature of the specific group of erythrocytes in two succeeding pulse-echo cycles divided by the time interval between pulse transmissions and multiplied by the speed of ultrasound wave propagation in tissue. Doppler systems measure the echo signature arrival time by comparing the echo with the transmit pulse to determine the phase. Although the Doppler method is a special case of time-domain methods, use of the term "Doppler" here includes the time-domain method.

Tissue: A bodily material, including blood, which will permit the propagation of ultrasonic wave energy through it, attenuating the ultrasonic energy by absorption, reflection, and scattering.

Transceiver: An ultrasound transducer that acts both for transmitting and for receiving.

Transducer: In ultrasound technology, a device that can convert an electrical voltage pulse into mechanical vibrations in the ultrasonic frequency range and can convert mechanical vibrations into electrical voltage oscillations.

Transverse: The heading which is perpendicular to the bisector of the angle formed by the sample volume at the vertex and arms passing through two ultrasonic receiving transducers respectively and which is in the plane of that angle.

Triphasic: The presence of three sounds in an arterial Doppler signal during systole of each cardiac cycle; often the first sound is associated with forward flow (away from the heart), the second with reverse flow, and the third with forward flow again (see monophasic, biphasic).

Ultrasound: Longitudinal mechanical vibrations in the frequency range between 1 MegaHertz and 30 MegaHertz which, in body tissues, have wavelengths between 1.5 millimeters and 0.05 millimeters.

us: Refers to microseconds, 1,000,000 us=1 second.

Vector Doppler: A pulse-echo velocity measuring device which can determine the heading of the velocity vector in tissue as well as the direction of travel along the vector and the magnitude of the velocity.

Velocity component: see Projection

Velocity Plane: A two-dimensional surface in concept on which the terminations of one or more velocity vectors can be plotted. The dimensions of the velocity plane are parallel to the dimensions in space, but the velocity dimensions have no spatial extent. Only velocity vectors may be plotted on the velocity plane. All vectors have their origins at the origin of the velocity plane and are directed radially to their terminations; thus a description of the termination is a complete description of the vector. $Vx(x,y,z,t,i)$, $Vy(x,y,z,t,i)$ describes a velocity vector within a sample volume at location x,y,z in space at time t with components in the velocity plane Vx representing the x heading in space and Vy representing the y heading in space; the subscript i indicates that more than one vector may be present in the volume at the same time.

Velocity Vector: A vector indicating the heading and speed of a group of erythrocytes in a sample volume.

Velocity Volume: An extension of the concept of the velocity plane into the third dimension. $Vx(x,y,z,t,i)$, $Vy(x,y,z,t,i)$, $Vz(x,y,z,t,i)$ describes a three-dimensional velocity vector within a sample volume located at x,y,z.

Video: any video display graphics system including: cathode ray tube, liquid crystal, and plasma computer display screens.

Waveform: A graphical plot of velocity, frequency, voltage along the ordinate and time along the abscissa.

REFERENCES

R. E. Daigle, C. W. Miller, M. B. Histad, F. D. McLeod, and D. E. Hokanson; *Nontraumatic Aortic Blood Flow Sensing by use of an Ultrasonic Esophageal Probe,* Journal of Applied Physiology 38: 1153–1160; 1975.

M. K. Eyer, M. A. Brandestini, D. J. Phillips, D. W. Baker; *Color digital echo/Doppler Image Presentation;* Ultrasound in Medicine and Biology, V.7, N.1, pp 21–31, Jan, 1981.

M. D. Fox; *True Volume Flow Measurement with Multiple Beam Ultrasound Doppler,* Proceedings of the Thirteenth Annual Northeast Bioengineering Conference, Institute of Electrical and Electronics Engineers Press, 2: 357–60; 1987.

D. L. Franklin, D. W. Baker, R. M. Ellis, R. F. Rushmer; *A Pulsed Ultrasonic Flowmeter;* Institute of Radio Engineers: Transactions in Medical Electronics V.6 P 204–206, 1959.

P. L. Hansen, G. Cross, and H. Light; *Beam-angle Independent Doppler Velocity Measurement in Superficial Vessels,* Clinical Blood Flow Measurement, J. P. Woodcock, Editor, Sector Publishing, 1974.

D. N. Ku, D. J. Phillips, D. P. Giddons, and D. E. Strandness, Jr, *Hemodynamics of the Normal Human Carotid Bifurcation: in Vitro and in Vivo Studies,* Ultrasound in Medicine and Biology, 11: 13–26; 1985.

R. C. Nealeigh, C. W. Miller, F. D. McLeod, Jr.; *Venous Ultrasound Catheter-tip Technique for Evaluation of Arterial Hemodynamics,* Journal of Applied Physiology, 41: 6 pp 946–952, Dec., 1976.

R. S. Reneman, T. vanMerode, P. Hick, A. P. Hoeks; *Cardiovascular Applications of Multi-gate Pulsed Doppler System;* Ultrasound in Medicine and Biology, V.12, N.5, pp 357–370, May 1986.

S. Satamura; *Ultrasonic Doppler Method for the Inspection of Cardiac Function;* Journal of the Acoustical Society of America: 29: 1181–1185, 1957.

P. A. Stonebridge and C. M. Brophy, *Spiral Laminar Flow in Arteries?,* The Lancet, V338, Nov. 30, 1991, pp 1360–1361.

D. E. Strandness, Jr., J. W. Kennedy, T. P. Judge, T. D. McLeod; *Transcutaneous Directional Flow Detection: a Preliminary Report,* American Heart Journal, 78: 1, pp 65–74 July 1969.

S. Uematsu; *Determination of Volume of Arterial Blood Flow by an Ultrasonic Device,* Journal of Clinical Ultrasound, v.9, pp. 209–216, June 1981.

W. Wei-qi and Y. Lin-xin, *A Double Beam Doppler Ultrasound Method for Quantitative Blood Flow Velocity Measurement,* Ultrasound in Medicine and Biology, V. 8, N. 4, pp 421–425, 1982.

T. L. Yearwood and K. B. Chanderin; *Physiological Pulsatile Flow Experiments in a Model of the Human Aortic Arch;* Journal of Biomechanics, V. 15, N.9, pp 683–704, 1984.

We claim:

1. A method for determining the velocity of blood flowing through a sample volume within a blood vessel in a body, which comprises directing toward the sample volume and toward a wall of the blood vessel a pulsed ultrasound transmitting transducer, directing toward the sample volume and the wall of the blood vessel two ultrasound receiving transducers located adjacent to the transmitting transducer, respectively, along arms of an angle having its apex at the sample volume, transmitting ultrasound pulses in a beam into the sample volume from the ultrasound transmitting transducer, receiving by the ultrasound receiving transducers ultrasonic echoes of such beam from blood flowing through the blood vessel, receiving by the ultrasound receiving transducers ultrasonic echoes of such beam from the wall of the blood vessel in motion, and displaying representations of the flow of blood through such sample volume and movement of the wall of the blood vessel in accordance with such ultrasonic echoes, in which the representation of the echoes from the wall of the blood vessel are separated from the representation of the echoes from the blood flowing through the blood vessel by backprojection.

2. The method defined in claim 1, including displaying the representation of the motion of the blood vessel wall separate from the representation of the motions of the blood flowing through the blood vessel.

3. In ultrasonic pulse-echo apparatus for determining the velocity of blood flowing through a sample volume within a blood vessel in a body including one transmitting ultrasonic transducer directed toward the sample volume and toward a wall of the blood vessel, means for generating pulsed ultrasound waves connected to the transmitting ultrasound transducer for projecting a pulsed ultrasound sound beam therefrom, two receiving ultrasonic transducers directed toward the sample volume and toward the wall of the blood vessel for receiving echoes of the pulsed ultrasound beam, means for processing signals produced by such ultrasonic echoes received by the receiving transducers and display means activated by the processing means for displaying representations of blood flowing through such sample volume and movement of the blood vessel wall, the improvement comprising means for separately identifying echoes from blood flowing in the blood vessel through the sample volume and echoes from the blood vessel wall in motion by backprojection, and means for displaying a representation of blood flowing through the blood vessel separate from a representation of the movement of the blood vessel wall.

* * * * *